United States Patent [19]

Haas et al.

[11] Patent Number: 4,523,030
[45] Date of Patent: Jun. 11, 1985

[54] BENZOPHENONES

[75] Inventors: Georges Haas, Binningen; Andreas von Sprecher, Oberwil; Pier G. Ferrini, Binningen, all of Switzerland

[73] Assignee: Ciba-Geigy Corporation, Ardsley, N.Y.

[21] Appl. No.: 618,152

[22] Filed: Jun. 7, 1984

[30] Foreign Application Priority Data

Jun. 15, 1983 [CH] Switzerland ............ 3270/83

[51] Int. Cl.³ ............................................. C07C 65/32
[52] U.S. Cl. .................... 562/460; 560/107; 560/52; 560/21; 560/10; 564/169; 260/501.1; 260/501.13; 260/465 F; 548/228
[58] Field of Search ............ 562/460, 21; 560/52, 560/10; 564/169; 424/308, 317, 324; 260/501.1, 501.13, 465 F

[56] References Cited

U.S. PATENT DOCUMENTS 3,953,500  4/1976  Noguchi et al. .................... 562/460
4,057,573  11/1977  Haas et al. ........................... 560/52
4,272,547  6/1981  Haas et al. ........................... 424/311

FOREIGN PATENT DOCUMENTS 2505106  8/1975  Fed. Rep. of Germany ...... 562/460

Primary Examiner—Paul J. Killos
Attorney, Agent, or Firm—Michael W. Glynn

[57] ABSTRACT

Substituted benzophenones of the formula

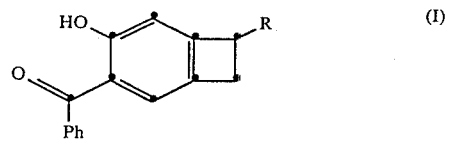

in which Ph represents unsubstituted or substituted phenyl and R represents free, esterified or amidated carboxy, have anti-inflammatory and/or analgesic properties and can be used as active ingredients in medicaments. They are manufactured, for example, as follows:

a compound or a mixture of compounds of the formula

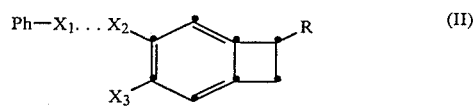

in which $X_1$ and $X_2$ together represent a group of the formula —C(=O)—O that is bonded via the carbonyl group to the radical Ph and $X_3$ represents hydrogen, or one of the radicals $X_1$ and $X_3$ represents a group of the formula —C(=O)—Z, the other represents hydrogen and $X_2$ represents a group R'O— in which R' represents hydrogen or a hydroxy-protecting group, is subjected to acid treatment and the primary product is decomposed solvolytically.

20 Claims, No Drawings

BENZOPHENONES

The invention relates to novel substituted benzophenones of the formula

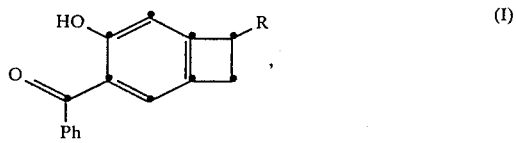

in which Ph represents unsubstituted or substituted phenyl and R represents free, esterified or amidated carboxy, and their salts, processes for their manufacture, the use of compounds of the formula I and their salts as active ingredients in or for the manufacture of pharmaceutical preparations, and to such pharmaceutical preparations.

Substituted phenyl is, for example, phenyl that is substituted, especially mono- or di-substituted, by lower alkyl, lower alkoxy, lower alkylthio, lower alkanoyloxy, halogen, trifluoromethyl, carboxy, lower alkoxycarbonyl, cyano and/or nitro.

Esterified carboxy is, for example, carboxy esterified by a lower aliphatic alcohol, such as lower alkoxycarbonyl.

Amidated carboxy has as amino group, for example, amino that is unsubstituted or mono- or di-substituted by lower aliphatic radicals and represents, for example, carbamoyl, N-mono- or N,N-di-lower alkylcarbamoyl or N,N-lower alkylene- or N,N-(aza)-, N,N-(oxa)- or N,N-(thia)-lower alkylene-carbamoyl.

Hereinbefore and hereinafter, lower organic radicals and compounds are preferably to be understood as those that have up to and including 7, especially up to and including 4, carbon atoms (C-atoms).

Lower alkyl is, for example, methyl, ethyl, propyl, isopropyl, butyl, isobutyl, secondary butyl or tertiary butyl, but may also be a pentyl, hexyl or heptyl radical.

Lower alkoxy is, for example, methoxy, ethoxy, propoxy, isopropoxy, butoxy, isobutoxy, secondary butoxy or tertiary butoxy, but may also be a pentyloxy, hexyloxy or heptyloxy radical.

Lower alkylthio is, for example, methylthio, ethylthio, propylthio, butylthio, isobutylthio, secondary butylthio or tertiary butylthio, but may also be a pentylthio, hexylthio or heptylthio group.

Lower alkanoyloxy is, for example, acetoxy, propionyloxy, butyryloxy or isobutyryloxy, also valeroyloxy, pivaloyloxy or caproyloxy.

Halogen is, for example, halogen having an atomic number of up to and including 35, such as fluorine or chlorine, and also bromine.

Lower alkoxycarbonyl is, for example, methoxy-, ethoxy-, propoxy-, isopropoxy-, butoxy-, isobutoxy-, secondary butoxy- or tertiary butoxy-carbonyl, but may also be a pentyloxy-, hexyloxy- or heptyloxy-carbonyl radical.

N-mono- or N,N-di-lower alkylcarbamoyl is, for example, N-methyl-, N,N-dimethyl-, N-ethyl-, N,N-diethyl-, N-propyl-, N-isopropyl-, N-butyl- or N-isobutyl-carbamoyl.

N,N-lower alkylene- or N,N-(aza)-, N,N-(oxa)- or N,N-(thia)-lower alkylene-carbamoyl has, for example, from 3 up to and including 8, especially 5 or 6, ring members and represents, for example, pyrrolidino-, piperidino-, piperazino- or N'-lower alkylpiperazino-, such as N'-methylpiperazino-, morpholino- or thiomorpholino-carbonyl.

Salts of compounds of the formula I are especially the salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper, aluminium or zinc salts, and also ammonium salts with ammonia or organic amines, such as optionally C-hydroxylated aliphatic amines, especially mono-, di- or tri-lower alkylamines, for example methyl-, ethyl-, dimethyl- or diethyl-amine, mono-, di- or tri-(hydroxy-lower alkyl)-amines, such as ethanol-, diethanol- or triethanol-amine, tris-(hydroxymethyl)-aminomethane or 2-hydroxy-tertiary butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine.

The novel compounds of the formula I have valuable pharmacological properties. In particular they exhibit a pronounced anti-nociceptive activity and an excellent inhibiting action on prostaglandin synthesis, and also a pronounced anti-inflammatory action. For example, in vivo, they prove effective in the phenyl-p-benzoquinone-induced writhing syndrome in mice according to J. Pharmacol. exp. Therap. 125, 237 (1959), and in the acetic acid-induced writhing syndrome in mice at peroral doses upwards from approximately 1.0 mg/kg, and likewise in the experimental carrageen in paw oedema and in the adjuvant arthritis test in rats at peroral doses upwards from 1 mg/kg and from 0.1 mg/kg, respectively. In vitro, for example in the test procedure according to Prostaglandins 7, 123 (1974), they exhibit a distinct inhibiting action on prostaglandin synthesis from arachidonic acid in a concentration range upwards from approximately 0.1 µM/liter.

The compounds of the formula I and their pharmaceutically acceptable salts are accordingly extremely suitable as the active ingredients in medicaments for the treatment of painful inflammatory disorders, especially of the rheumatic type, such as chronic arthritis.

The invention relates especially to compounds of the formula I in which Ph represents phenyl that is unsubstituted or substituted by lower alkyl, lower alkoxy, lower alkylthio, lower alkanoyloxy, halogen, trifluoromethyl, carboxy, lower alkoxycarbonyl, cyano and/or nitro, and R represents carboxy, carboxy esterified by a lower aliphatic alcohol, or carbamoyl having as amino group amino that is unsubstituted or mono- or di-substituted by lower aliphatic radicals, and their salts, especially pharmaceutically acceptable salts, with bases.

The invention relates more especially to compounds of the formula I in which Ph represents phenyl that is unsubstituted or mono- or di-substituted by lower alkyl, lower alkoxy, lower alkanoyloxy, halogen, trifluoromethyl, cyano and/or nitro, and R represents carboxy, carboxy esterified by a lower aliphatic alcohol, such as lower alkoxycarbonyl, or carbamoyl having as amino group amino that is unsubstituted or mono- or di-substituted by lower aliphatic radicals, such as carbamoyl, N-mono- or N,N-di-lower alkylcarbamoyl or N,N-lower alkylene- or N,N-(aza)-lower alkylene-, N,N-(oxa)-lower alkylene- or N,N-(thia)-lower alkylene-carbamoyl, and their salts, especially pharmaceutically acceptable salts, with bases.

The invention relates especially to compounds of the formula I in which Ph represents phenyl that is unsubstituted or mono- or di-substituted by lower alkyl having up to and including 4 C-atoms, such as methyl, lower alkoxy having up to and including 4 C-atoms, such as methoxy, lower alkanoyloxy having up to and including 4 C-atoms, such as acetoxy, halogen having an atomic number of up to and including 35, such as fluorine or bromine, and/or trifluoromethyl, and R represents carboxy, lower alkoxycarbonyl having up to and including 5 C-atoms, such as methoxy- or ethoxycarbonyl, or carbamoyl or N-lower alkylcarbamoyl having up to and including 5 C-atoms, such as carbamoyl or N-methylcarbamoyl, and their salts, especially pharmaceutically acceptable salts, with bases.

The invention relates especially also to compounds of the formula I in which Ph represents phenyl that is unsubstituted or mono- or di-substituted, especially in the 2- and/or 4-position, by lower alkyl having up to and including 4 C-atoms, such as methyl, lower alkylthio having up to and including 4 C-atoms, such as methylthio, lower alkoxycarbonyl having up to and including 4 C-atoms in the lower alkoxy moiety, such as methoxycarbonyl, halogen having an atomic number of up to and including 35, such as fluorine, chlorine or bromine, and/or cyano, and R represents carboxy or carbamoyl, also lower alkoxycarbonyl having up to and including 4 C-atoms in the lower alkoxy moiety, such as methoxycarbonyl, and their salts, especially pharmaceutically acceptable salts, with bases.

The invention relates first and foremost to compounds of the formula I in which Ph represents phenyl that is mono-substituted, especially in the 2-position, or di-substituted, especially in the 2- and 4-positions, by lower alkyl having up to and including 4 C-atoms, such as methyl, or preferably by halogen having an atomic number of up to and including 35, such as fluorine, chlorine or bromine, and R represents carboxy or carbamoyl, also lower alkoxycarbonyl having up to and including 4 C-atoms in the lower alkoxy moiety, such as methoxycarbonyl, and their salts, especially pharmaceutically acceptable salts, with bases.

The invention relates specifically to the compounds of the formula I mentioned in the Examples and to their pharmaceutically acceptable salts.

The compounds of the formula I can be manufactured according to methods known per se, for example as follows: a compound or a mixture of compounds of the formula

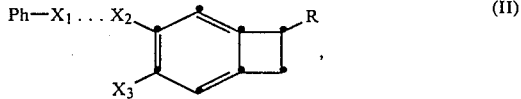

(II)

in which $X_1$ and $X_2$ together represent a group of the formula —C(=O)—O— that is bonded via the carbonyl group to the radical Ph and $X_3$ represents hydrogen, or one of the radicals $X_1$ and $X_3$ represents a group of the formula —C(=O)—Z, the other represents hydrogen and $X_2$ represents a group R'O—, in which R' represents lower alkyl, for example methyl, or a hydroxy-protecting group R'', such as α-aryl-lower alkyl, for example benzyl, tri-lower alkylsilyl, for example trimethylsilyl, or a group of the formula Ph—C(=O)—, or, if $X_3$ represents hydrogen, R' may also represent hydrogen, and Z represents reactive esterified hydroxy, for example halogen, especially chlorine, or, if $X_1$ represents a group —C(=O)—Z, it represents a group Ph—C(=O)—O—, is subjected to acid treatment, the primary product is decomposed solvolytically without being isolated and, if desired, the compound obtainable according to the process is converted into a different compound of the formula I and/or a compound obtainable according to the process is converted into a salt, or a salt obtainable according to the process is converted into the free compound or into a different salt.

Acids suitable for the acid treatment are, for example, complex protonic acids, such as sulphuric, pyrosulphuric, phosphoric, pyrophosphoric or polyphosphoric acid; or Lewis acids, such as complex metal halides of the formula $M^nY_n$ (III) in which M represents an n-valent, coordinatively unsaturated metal cation of the group IIb, IIIa, IIIb, IVb, Va or VIIIb of the Periodic Table of Elements, for example the zinc$^{II}$, boron$^{III}$, aluminium$^{III}$, gallium$^{III}$, tin$^{IV}$, titanium$^{IV}$, antimony$^V$ or iron$^{III}$ or iron$^{VI}$ ion, and Y represents a halogen atom having an atomic number of up to and including 35, such as fluorine or chlorine.

The acid treatment is carried out in customary manner, for example in a solvent that is inert towards the reactants, such as an alkane, for example hexane, aromatic substances, for example benzene, toluene or the like, haloalkane, for example tetrachloromethane, dichloromethane or trichloroethane, or carbon disulphide, if necessary while cooling or heating, for example in a temperature range of approximately from −5° to +30° C., and/or under an inert gas, such as nitrogen.

The solvolytic decomposition of the primary product is carried out in customary manner, for example by hydrolysis, that is to say treatment with water, but also by treatment with organic compounds containing hydroxy groups, such as alcohols, for example lower alkanols, or carboxylic acids, for example lower alkanoic acids, if necessary in the presence of acidic solvolysis agents, such as mineral acids, for example hydrochloric acid or sulphuric acid, or ammonium salts of such acids, for example ammonium chloride, if appropriate while cooling, for example in a temperature range of approximately from −15° to +20° C., and/or under an inert gas, such as nitrogen.

A preferred method is, for example, characterised in that one of the mentioned complex protonic acids and/or the anhydrides thereof or a metal halide of the formula $M^nY_n$, preferably zinc chloride, aluminium trichloride, tin tetrachloride or antimony pentachloride, in which Y and n have the meanings given above, is caused to act on a mixture of compounds of the formulae IIa and IIb or on a compound of the formula IIc

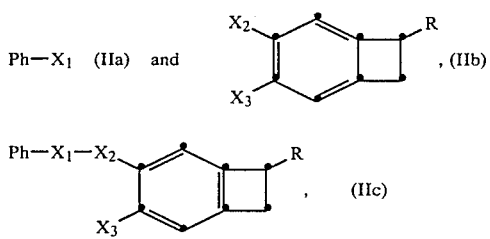

In an especially preferred form of this process, there are used as starting materials, for example, compounds of the formulae Ph—C(=O)—Hal (IId) and 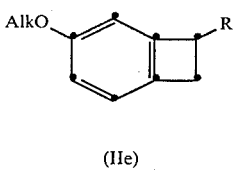

(IIe)

or a compound of the formula

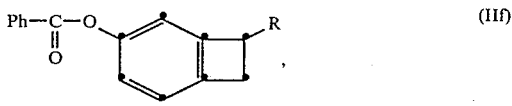 (IIf)

in which Hal represents halogen, for example chlorine, and Alk represents lower alkyl, and preferably aluminium trichloride is used as metal halide.

The intermediates of the formula II can be manufactured, for example, by cyclising a compound of the formula

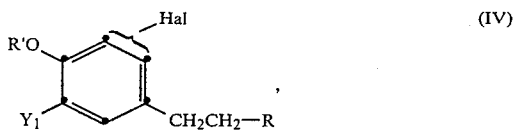 (IV)

or a phenolate salt and optionally a carboxylate salt thereof, in which $Y_1$ represents hydrogen or optionally esterified carboxy, such as carboxy or lower alkoxycarbonyl, in customary manner, for example by means of an alkali metal amide, such as potassium amide in ammonia or lithium N,N-diethylamide in tetrahydrofuran, and, if desired, O-acylating a reaction product of the formula IIb ($X_2$=OH, $X_3$=H) by means of a compound of the formula IId or, in a reaction product IIb ($X_2$=OR″, $X_3$=optionally esterified carboxy), hydrolysing esterified carboxy to carboxy and converting carboxy, for example by means of thionyl chloride, into halocarbonyl.

The compounds of the formula I can also be manufactured by, in a compound of the formula

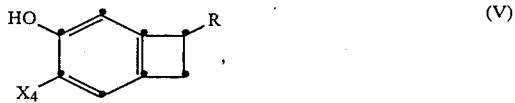 (V)

in which $X_4$ represents a radical that can be converted by oxidation or solvolysis into a group of the formula —C(=O)—Ph, oxidising or solvolysing $X_4$ to the desired group of the formula —C(=O)—Ph and, if desired, converting the compound obtainable according to the process into a different compound of the formula I and/or converting a compound obtainable according to the process into a salt or converting a salt obtainable according to the process into the free compound or into a different salt.

Radicals that can be converted by oxidation into a group of the formula —C(=O)—Ph are, for example, those of the formula —C($X_5X_6$)—Ph in which $X_5$ represents hydrogen and $X_6$ represents hydrogen or optionally etherified or esterified hydroxy, such as hydroxy, lower alkoxy, halogen, lower alkanoyloxy or optionally substituted benzoyloxy.

The oxidation is carried out in customary manner by reaction with a suitable oxidising agent, advantageously in a solvent or diluent, if necessary while cooling or heating, for example at approximately from 0° to 100° C., in a closed vessel and/or under an inert gas, such as nitrogen. Suitable oxidising agents are, for example, oxygen, preferably in the presence of a catalyst, such as a silver, manganese, iron or cobalt compound, per compounds, such as hydrogen peroxide, metal peroxides, for example nickel peroxide, percarbonic acid and its salts or organic peracids, for example m-chloroperbenzoic acid, phthalomonoperacid or peracetic acid, or their salts, oxidising oxy-acids or their salts or anhydrides, such as hypohalogenous acids and their salts, for example sodium hypochlorite, halic acids and their salts, for example iodic acids, periodic acids, potassium iodate, sodium periodate or potassium chlorate, nitric acid or nitrous acid and their salts and anhydrides, for example potassium nitrate, sodium nitrite, nitric oxide, dinitrogen trioxide or nitrogen dioxide, or oxidising heavy metal compounds, such as chromium(VI), chromium(IV), manganese(IV), manganese(VII), silver(II), copper(II), mercury(II), vanadium(V) or bismuth(II) compounds, for example pyridinium dichromate, potassium dichromate, chromium trioxide, manganese dioxide, potassium permanganate, silver(II) oxide, copper(II) oxide, mercury oxide or bismuth oxide. Inert solvents are, for example, solvents that are inert towards the particular oxidising agent used, such as water, ketones, for example acetone, carboxylic acids and their anhydrides, for example acetic acid or acetic anhydride, halogenated hydrocarbons, for example di- or tetra-chloromethane, or aromatic or heteroaromatic substances, for example benzene or pyridine, or mixtures thereof.

Further suitable oxidising agents are, for example, N-halo-, preferably N-chloro- or N-bromo-, dicarboxylic acid imides, for example N-chloro- or N-bromo-lower alkane-dicarboxylic acid imides, such as N-chloro- or N-bromo-succinimide, in the presence of thio-ethers, such as aliphatic and/or araliphatic sulphides, for example lower alkylthioalkanes, such as dimethyl sulphide, or lower alkylthio-lower alkylbenzenes, such as α-methylthiotoluene. Further selective oxidising agents for hydroxymethylene are, for example, ketones, such as di-lower alkyl ketones, for example acetone or methyl ethyl ketone, optionally unsaturated cycloalkanones, preferably those having from 5 to 7 ring members, for example cyclopentanone, cyclohexanone, cyclohex-2-enone or quinones. The reaction with ketones is advantageously carried out in the presence of a catalytic agent and using an excess of the oxidising ketone. Catalytic agents suitable for this purpose are, for example, alcoholates, preferably lower alkoxides or phenolates of coordinatively unsaturated metals, such as magnesium, boron or, especially, aluminium, for example aluminium phenolate or isopropoxide.

Radicals that can be converted by solvolysis into a group of the formula —C(=O)—Ph are, for example, radicals —C(=O)—Ph that are functionally modified at the carbonyl group, for example radicals of the formula —C($X_5X_6$)—Ph in which $X_5$ and $X_6$, independently of one another, each represents hydroxy etherified or esterified by a monohydric alcohol, such as lower alkoxy, optionally substituted phenoxy, halogen, lower alkanoyloxy or optionally substituted benzyloxy, mercapto optionally etherified by a monovalent mercaptan, such as mercapto, lower alkylthio or optionally substituted phenylthio, or optionally substituted amino, such as amino, N-mono- or N,N-di-lower alkylamino, or optionally substituted anilino, or they together represent hydroxy or mercapto etherified by a dihydric alcohol or mercaptan, such as lower alkylenedioxy, for example ethylenedioxy or 1,3-propylenedioxy, lower alkylenedithio, for example ethylenedithio or 1,3-propylenedithio, or optionally substituted 1,2-phenylenedioxy or 1,2-phenylenedithio, or thioxo or optionally substituted imino, such as lower alkylimino, or optionally substituted anilo or benzylimino.

The solvolytic conversion of groups $X_4$ into groups of the formula $—C(=O)—Ph$ is carried out, for example, by hydrolysis. The hydrolysis is carried out in customary manner, if necessary in the presence of a solvent or diluent and/or an auxiliary, while cooling or heating, for example in a temperature range of approximately from 0° to 100° C., in a closed vessel and/or under an inert gas. Suitable solvents or diluents are, for example, water-miscible solvents, such as alcohols or ketones, for example lower alkanols or di-lower alkyl ketones, also N,N-di-lower alkylamides or N-lower alkyl lactams, for example dimethylformamide or N-methylpyrrolidone, also di-lower alkyl sulphoxides, for example dimethyl sulphoxide, and also dioxan or acetic acid. Auxiliaries are, for example, acidic or basic solvolysis agents, such as protonic acids, for example mineral acids, inter alia hydrochloric, hydrobromic or hydriodic acid, sulphuric acid or phosphoric acid, or organic carboxylic acids, for example lower alkanoic acids, inter alia acetic acid, or bases, such as alkali metal or alkaline earth metal hydroxides, for example sodium, potassium or calcium hydroxide, alkali metal carbonates, inter alia sodium or potassium carbonate, or nitrogen bases, such as ammonia, and, in the case of transesterification, also alcoholates, such as alkali metal lower alkoxides, for example sodium methoxide. When using as starting materials optionally thioketalised thioxo compounds, for example of the formula V, in which $X_5$ and $X_6$ each represent etherified mercapto or together represent thioxo, there come into consideration as further auxiliaries heavy metal compounds, for example mercury compounds, or customary oxidising agents, for example N-chlorosuccinimide.

The starting materials can be manufactured according to methods known per se.

Intermediates of the formula V in which $X_5$ represents hydrogen and $X_6$ represents hydroxy are obtained, for example, as follows: compounds of the formulae

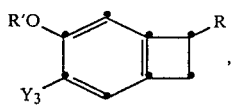

Ph—$Y_2$ (VI) and
in which R'O represents free hydroxy or preferably hydroxy that is in salt form, for example in alkali or alkaline earth metal salt form, or that is protected by a hydroxy-protecting group R'', such as tri-lower alkylsilyl, for example trimethylsilyl, or α-aralkyl, for example benzyl, one of the radicals $Y_2$ and $Y_3$, preferably $Y_2$, represents a metallic radical, such as an alkali metal atom or a halomagnesium group, and the other, preferably $Y_3$, represents formyl, are reacted with one another in customary manner, for example in an ethereal solvent, such as tetrahydrofuran, and, if appropriate, the protecting group R'' is removed in customary manner. It is possible to obtain from resulting compounds of the formula V in which $X_4$ represents a group $Ph(X_5)(X_6)—$, $X_5$ represents hydrogen and $X_6$ represents hydroxy, by customary esterification by means of a corresponding carboxylic acid anhydride, also the esters thereof with organic carboxylic acids. Compounds of the formula V in which $X_5$ and $X_6$ each represent halogen or hydrogen or together represent optionally substituted imino can also be obtained in analogous manner by using as starting materials compounds of the formulae VI and VII in which $Y_2$ or $Y_3$ represents a metallic radical and $Y_3$ or $Y_2$, as the case may be, represents a trihalomethyl, halomethyl or optionally N-substituted α-haloiminomethyl group or a cyano group.

Intermediates of the formula V in which $X_4$ represents a group $—C(X_5)(X_6)—Ph$ and $X_5$ and $X_6$ each represent halogen or together represent imino can, however, also be obtained by treating a compound or a mixture of compounds of the formula II, in which one of the radicals $X_1$ and $X_3$ represents trihalomethyl or cyano and the other represents hydrogen and $X_2$ represents etherified hydroxy, or $X_1$ and $X_2$ represent a group of the formula $—C(=NH)—O—$ bonded via the iminomethyl group to Ph, with a complex protonic acid, such as sulphuric acid or polyphosphoric acid, or, especially, with a coordinatively unsaturated metal halide, such as aluminium trichloride.

Intermediates of the formula V in which $X_5$ and $X_6$ each represent hydroxy etherified by a monohydric alcohol or mercaptan or together represent hydroxy etherified by a dihydric alcohol or mercaptan, can also be manufactured by reacting, in customary manner, a compound of the formula

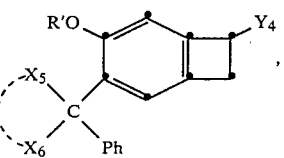

in which R'O represents free hydroxy or preferably hydroxy that is in salt form, for example in alkali metal or alkaline earth metal salt form, or that is protected by a hydroxy-protecting group R'', such as tri-lower alkylsilyl, for example trimethylsilyl, or α-aralkyl, for example benzyl, and $Y_4$ represents halogen, for example with magnesium and then with carbon dioxide or a haloformic acid derivative, for example of the formula Hal—R (IX), or with a metal carbonyl, such as iron or nickel tetracarbonyl, and, if appropriate, removing the protecting group R''. Compounds of the formula V in which $X_5$ represents etherified hydroxy or mercapto and $X_6$ represents hydrogen can also be obtained by this method.

The starting materials can be obtained, for example, by customary ketalisation, for example by means of an orthoformic acid tri-lower alkyl ester, of a compound of the formula

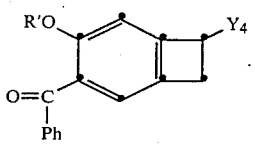 (X)

The compounds of the formula I can also be manufactured by treating a compound of the formula

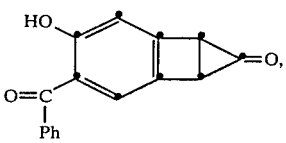 (XI)

or a phenolate salt thereof, with water, an alcohol or ammonia or an amine having at least one hydrogen atom, if necessary isolating the isomer of the formula I from a mixture of isomers obtainable according to the process and, if desired, converting the compound obtainable according to the process into a different compound of the formula I and/or converting a compound obtainable according to the process into a salt or converting a salt obtainable according to the process into the free compound or into a different salt.

The operation is carried out in customary manner, if necessary in the presence of a base, such as an alkali metal hydroxide, alcoholate or amide, or by using an alcohol, ammonia or the amine in the form of a metal salt, for example an alkali metal salt, advantageously in a solvent or diluent that may be inert towards the reactants or that may consist of an excess of water, alcohol or amine, if necessary while heating, for example at approximately from 20° to 100° C., and/or under an inert gas, such as nitrogen.

The starting materials of the formula XI are advantageously manufactured in situ and further reacted without being isolated. The starting material used is, for example, a compound of the formula

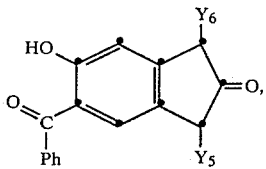 (XII)

or a phenolate and an enolate salt thereof, in which one of the radicals $Y_5$ and $Y_6$ represents reactive esterified hydroxy, such as halogen, for example chlorine, bromine or iodine, or sulphonyloxy, such as lower alkanesulphonyloxy or optionally substituted benzene- or fluoro-sulphonyloxy, for example methane-, ethane-, benzene-, p-toluene- or fluoro-sulphonyloxy, and the other represents hydrogen, and this starting material is reacted in the presence of a suitable base with water, an alcohol, ammonia or an amine. Suitable bases are, for the reaction with water, for example alkali metal hydroxides, such as sodium or potassium hydroxide, for the reaction with an alcohol, for example metal alcoholates, preferably alkali metal alcoholates, of the same, such as the sodium or potassium alcoholate thereof, and, for the reaction with ammonia or an amine, corresponding alkali metal amides, for example sodium or potassium amides.

The reaction can, however, also be carried out by first of all converting the compound of the formula XII by treatment with a base, as which there come into consideration, apart from those mentioned, also metal bases, that is to say organometallic compounds derived from hydrocarbons, such as lower alkyl- or phenyl-lithium compounds, lower alkyl- or phenyl-magnesium halides and the like, into the corresponding salt which cyclises spontaneously to form a compound of the formula XI and then further reacting this compound in the manner indicated without isolating it.

The compounds of the formula I can also be manufactured by reducing a compound of the formula

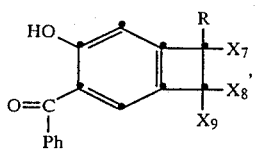 (XIII)

or a phenolate and/or carboxylate salt thereof, in which at least one of the radicals $X_7$ and $X_8$ represents optionally etherified or esterified hydroxy and a radical $X_7$ or $X_8$ that does not represent optionally etherified or esterified hydroxy represents hydrogen, as does $X_9$, or $X_7$ represents hydrogen and $X_8$ and $X_9$ represent optionally functionally modified oxo, and, if desired, converting the compound obtainable according to the process into a different compound of the formula I and/or converting a compound obtainable according to the process into a salt or converting a salt obtainable according to the process into the free compound or into a different salt.

Etherified or esterified hydroxy is, for example, lower alkoxy, optionally substituted phenoxy, halogen, such as chlorine, bromine or iodine, lower alkanoyloxy or optionally substituted benzoyloxy. Functionally modified oxo is, for example, thioxo, optionally substituted imino, such as imino, or anilo, ketalised or thioketalised oxo, for example bis-lower alkoxy, such as bismethoxy or bisethoxy, lower alkylenedioxy, such as ethylenedioxy or 1,3-propylenedioxy, bis-lower alkylthio, such as bismethylthio, or lower alkylenedithio, such as ethylenedithio.

The reduction is carried out in customary manner, for example by treatment with catalytically activated or nascent hydrogen, such as hydrogen in the presence of a hydrogenation catalyst, for example platinum, nickel or palladium or a compound of these metals, inter alia platinum, platinum oxide, Raney nickel or palladium, or with nascent hydrogen produced by the acid treatment of non-noble metals or metal alloys, for example zinc, sodium amalgam, amalgamated aluminium and the like. Compounds of the formula XIII ($X_8+X_9=$oxo) can also advantageously be reduced by treatment with hydrazine in the presence of a base, such as an alkali metal hydroxide or alcoholate, advantageously while heating, for example at approximately from 130° to 250° C. Here it is also possible to use as starting materials compounds of the formula XIII in which $X_8$ and $X_9$ together represent functionally modified oxo (apart from ketalised or thioketalised oxo). The oxo compound must first of all be freed from ketals or thioketals, for example by acid hydrolysis.

If $X_7$ represents a free hydroxy group and $X_8$ and $X_9$ represent hydrogen, it is also possible to use as reducing agent an aqueous suspension of phosphorus and iodine, hydriodic acid, tin(II) chloride or an alkali metal sulphite or dithionite, for example sodium sulphite or dithionite.

The starting materials of the formula XIII can be manufactured according to methods known per se, for example by introducing the group of the formula Ph—C(=O)— in customary manner, for example in the manner indicated for the compounds of the formulae II, into a compound of the formula

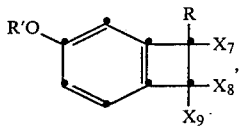 (XIV)

in which R' represents hydrogen, lower alkyl, such as methyl, or a hydroxy-protecting group R'', such as α-aralkyl, for example benzyl, or tri-lower alkylsilyl, for example trimethylsilyl, or a group of the formula Ph—C(=O)—.

Compounds of the formula XIV in which $X_7$ represents hydrogen and $X_8$ and $X_9$ represent oxo can for their part be obtained, for example, by the ring closure of a compound of the formula

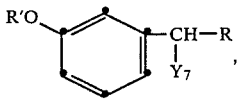 (XV)

in which $Y_7$ represents optionally esterified carboxy or carboxy optionally anhydridised by a mineral acid, such as carboxy, lower alkoxycarbonyl or chlorocarbonyl, for example under the conditions of the condensation or rearrangements of compounds of the formula II, or, starting from a compound of the formula

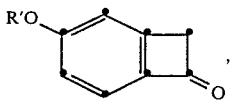 (XVI)

by conversion into the enolate salt, for example by means of a metal base, such as sodium hydride, and subsequent reaction with a reactive carbonic acid derivative, such as carbon dioxide, a carbonic acid diester, haloformic acid ester or carbamoyl chloride, or by α-halogenation, for example with bromine, N-bromosuccinimide or N-chlorosuccinimide, reaction with an alkali metal cyanide and subsequent solvolysis of the cyano group to form a group R. In an analogous manner, compounds of the formula XIV ($X_7$, $X_8$, $X_9$=hydroxy; =H) are obtained by conversion of an aldehyde of the formula

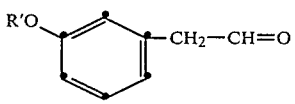 (XVII)

into a salt, reaction with a reactive carbonic acid derivative to form a compound of the formula

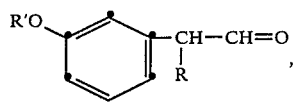 (XVIII)

and subsequent ring closure. The group Ph—C(=O)— is then introduced in the manner indicated for compounds of the formula II.

Compounds of the formula XIII in which $X_7$ represents hydroxy and $X_8$ and $X_9$ represent hydrogen can also be manufactured by reacting a compound of the formula

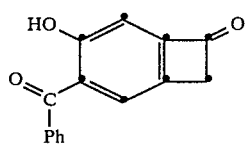 (XIX)

in customary manner with aqueous alkali metal cyanide and, in the resulting α-hydroxynitrile of the formula

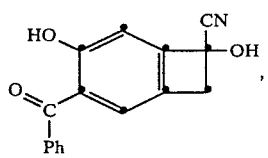 (XX)

converting the cyano group in customary manner into optionally esterified or amidated carboxy R.

The compounds of the formula I can also be manufactured by, in a functional carboxy derivative thereof that is other than an ester or amide of the formula I, or in a salt thereof, converting the functionally modified carboxy group by solvolysis into an optionally esterified or amidated carboxy group and, if desired, converting a compound obtainable according to the process into a different compound of the formula I and/or converting a free compound obtainable according to the process into a salt or converting a salt obtainable according to the process into the free compound or into a different salt, and/or separating a mixture of isomers obtainable according to the process into the components.

Functional carboxy derivatives of this type are, for example, acid anhydrides, such as mixed anhydrides with carboxylic acids, such as lower alkanoic acids, for example with formic or acetic acid, or inorganic acids, such as hydrohalic acids, for example with hydrochloric acid, or hydrocyanic acid, or internal anhydrides, that is to say ketones, ortho-anhydrides, such as corresponding trihalomethyl, for example trichloromethyl or tribromomethyl, compounds, ortho-anhydride esters, such as dihalomethanol esters corresponding to esters of the formula I, for example lower alkoxydihalomethyl compounds, ortho-esters, such as ortho-esters corresponding to esters of the formula I, for example tri-lower alkoxymethyl compounds, imino ethers and amidines, such as imino ethers, imino esters and amidines corresponding to esters or amides of the formula I, or lower alkyleneimino ethers, such as imino ethers containing as functionally modified carboxy group 4,4- or 5,5-dimethyloxazin-2-yl or 4,6,6-trimethyldihydrooxazin-2-yl, mono- and di-thiocarboxylic acids and their esters and amides, but preferably nitriles.

Functional carboxy derivatives of compounds of the formula I are, for example, compounds of the formula

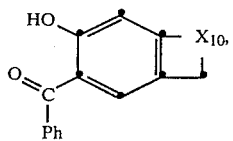

in which $X_{10}$ represents a group of the formula $>CH-X_{11}$ or $>C=X_{12}$, $X_{11}$ represents functionally modified carboxy other than esterified or amidated carboxy R, such as anhydridised carboxy, trihalomethyl, etherified hydroxydihalomethyl, for example lower alkoxydichloromethyl, etherified trihydroxymethyl, for example tri-lower alkoxymethyl, etherified or esterified C-hydroxyiminomethyl, for example C-lower alkoxyiminomethyl, 4,4- or 5,5-dimethyloxazin-2-yl, 4,6,6-trimethyldihydrooxazin-2-yl or C-haloiminomethyl, optionally etherified or amidated mono- or di-thiocarboxy or cyano, and $X_{12}$ represents optionally functionally modified, such as acetalised or thio-acetalised, carbonyl, for example 1,3-dithian-2-ylidene.

The solvolysis is carried out in customary manner, for example by hydrolysis, alcoholysis, that is to say reaction with an alcohol, or ammonolysis or aminolysis, that is to say reaction with ammonia or with an amine having at least one hydrogen atom.

By hydrolysis, it is possible, for example, to convert one of the mentioned functional carboxy derivatives, and also esters and amides, into the carboxylic acids of the formula I (R=carboxy), and also to convert ortho-anhydride esters, ortho-esters and imino ethers into esters of the formula I (R=esterified carboxy) and to convert imino esters, amidines and nitriles into amides (R=amidated carboxy).

The hydrolysis is carried out in customary manner by treatment with water, if necessary in the presence of a hydrolysis agent, in a solvent or diluent, while cooling or heating, for example in a temperature range of approximately from 0° to 100° C., and/or under an inert gas, such as nitrogen. Hydrolysis agents are, for example, acidic or basic hydrolysis agents. Acidic hydrolysis agents are, for example, protonic acids, such as mineral acids, for example sulphuric acid, such as hydrohalic acids, for example hydrochloric, hydrobromic or hydriodic acid, or phosphoric acid, sulphonic acids, such as p-toluenesulphonic acid, or carboxylic acids, for example lower alkanoic acids, for example formic or acetic acid. Basic hydrolysis agents are, for example, hydroxides or carbonates of alkali metals and alkaline earth metals, for example sodium or potassium hydroxide, sodium or potassium carbonate or calcium hydroxide, or nitrogen bases, such as ammonia or organic amines, such as tri-lower alkylamines, pyridine or benzyltriethylammonium hydroxide. Solvents or diluents are, for example, water-miscible organic solvents, such as alcohols, for example lower alkanols, ketones, for example di-lower alkyl ketones, N,N-di-lower alkyl-lower alkanoic acid amides or N-lower alkyl-lower alkanoic acid lactams, for example dimethylformamide or N-methylpyrrolidone, or di-lower alkyl sulphoxides, for example dimethyl sulphoxide.

By alcoholysis it is possible, for example, to convert acid anhydrides, such as mixed anhydrides with carboxylic acids or inorganic acids, or ketenes, into esters of the formula I (R=esterified carboxy).

The alcoholysis is carried out in customary manner, if necessary in the presence of a condensation agent, in a solvent, while cooling or heating, for example in a temperature range of approximately from 0° to 150° C., in a closed vessel and/or under an inert gas, such as nitrogen. Condensation agents are, for example, acidic condensation agents, such as mineral acids, for example sulphuric acid or hydrohalic acids, such as hydrochloric, hydrobromic or hydriodic acid, or, especially, basic condensation agents, such as alkali metal alcoholates of corresponding alcohols, such as alkali metal lower alkoxides, for example sodium methoxide or sodium ethoxide, alkali metal hydroxides or carbonates, for example sodium or potassium hydroxide or potassium carbonate, or tertiary nitrogen bases, such as heteroaromatic nitrogen bases, for example pyridine, or tri-lower alkylamines, for example triethylamine. There come into consideration as solvents, apart from an excess of the particular alcohol or of the tertiary nitrogen base used, for example ethers, such as di-lower alkyl or lower alkylene ethers, for example diethyl ether, tetrahydrofuran or dioxan, hydrocarbons, such as aromatic or araliphatic hydrocarbons, for example benzene, toluene or xylenes, N,N-di-lower alkyl-lower alkanoic acid amides or N-lower alkyl-lower alkanoic acid lactams, for example dimethylformamide or N-methylpyrrolidone, or di-lower alkyl sulphoxides, for example dimethyl sulphoxide.

By ammonolysis or aminolysis, it is possible, for example, to convert acid anhydrides, such as mixed anhydrides with carboxylic acids or mineral acids, and ketenes, into amides of the formula I (R=amidated carboxy).

The ammonolysis or aminolysis is carried out in customary manner, if necessary in the presence of a condensation agent, in a solvent, while cooling or heating, for example in a temperature range of approximately from 0° to 150° C., in a closed vessel and/or under an inert gas, such as nitrogen. Condensation agents are, for example, basic condensation agents, such as alkali metal hydroxides or carbonates, for example sodium or potassium hydroxide or potassium carbonate, or tertiary organic nitrogen bases, such as heteroaromatic nitrogen bases, for example pyridine, or tri-lower alkylamines, for example triethylamine. As solvents, apart from an excess of an organic amine when amine is used, there come into consideration, for example, ethers, such as di-lower alkyl or lower alkylene ethers, for example diethyl ether, tetrahydrofuran or dioxan, hydrocarbons, such as aromatic or araliphatic hydrocarbons, for example benzene, toluene or xylenes, N,N-di-lower alkyl-lower alkanoic acid amides or N-lower alkyl-lower alkanoic acid lactams, for example dimethylformamide or N-methylpyrrolidone, or di-lower alkyl sulphoxides, for example dimethyl sulphoxide.

The compounds of the formula I can also be manufactured by, in a compound of the formula

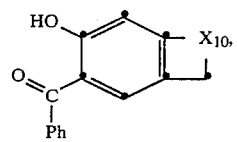

in which $X_{10}$ represents a group of the formula $>CH-X_{11}$ and $X_{11}$ represents a radical that can be converted by oxidation into a group R, oxidising the radical $X_{11}$ to a group R and, if desired, converting a compound obtainable according to the process into a different compound of the formula I and/or converting a free compound obtainable according to the process into a salt or converting a salt obtainable according to the process into the free compound or into a different salt.

Radicals that can be converted by oxidation into groups R are, for example, acyl groups that are derived from organic carboxylic acids and can be oxidised to carboxy R, optionally substituted lower alkenyl or lower alkynyl radicals, such as lower alkenyl or lower alkynyl radicals containing a phenyl radical, or methyl, aminomethyl or hydroxymethyl, and also 2-furyl that is optionally substituted in the 5-position, such as 2-furyl containing di-lower alkoxymethyl. Acyl $X_{11}$ that is derived from organic carboxylic acids and can be oxidised to carboxy is, for example, lower alkanoyl or lower alkenoyl that is optionally substituted, for example in the 2-position by free or functionally modified carboxy, halogen or oxo and/or in the 2-and/or 3-position by hydroxy, and, in a position higher than the 2-position, optionally additionally by optionally esterified carboxy or a phenyl group, such as lower alkanoyl, especially formyl that is optionally in hydrate form, enol ether form, for example in the form of an enol ether with an alcohol of the formula $R_o$—OH in which $R_0$ represents a hydrocarbon radical, such as lower alkyl, in acetal form, for example in the form of di-lower alkyl or lower alkylene acetal, or acylate form, for example in the form of a di-lower alkanoyloxy or dihalomethyl group; also acetyl, propionyl, pivaloyl and the like; optionally functionally modified, such as esterified or amidated oxalo, for example oxalo or lower alkoxy-oxalyl; 2-mono-, 2,2-di- or 2,2,2-tri-halo-lower alkanoyl, for example mono-, di- or tri-chloroacetyl, mono-, di- or tri-bromoacetyl or mono-, di- or tri-iodoacetyl; 2-oxo-lower alkanoyl or 2-oxophenyl-lower alkanoyl, such as pyruvoyl or benzoylcarbonyl; 2-hydroxy-lower alkanoyl, for example glycoloyl or optionally functionally modified, for example esterified or amidated, 3-carboxy-2,3-dihydroxypropionyl, such as tartrono or lower alkoxytartronoyl, or lower alkenoyl optionally substituted by a phenyl group, for example acryloyl, methacryloyl, crotonyl, cinnamoyl and the like. Further groups $X_{11}$ are etherified hydroxymethyl groups, such as lower alkoxymethyl, that can be oxidised to esterified carboxy, such as lower alkoxycarbonyl, R.

The oxidation is carried out in customary manner by reaction with a suitable oxidising agent, advantageously in a solvent or diluent, if necessary while cooling or heating, for example at approximately from 0° to 100° C., in a closed vessel and/or under an inert gas, such as nitrogen. Suitable oxidising agents are, for example, oxygen, preferably in the presence of a catalyst, such as a silver, manganese, iron or cobalt compound, per compounds, such as hydrogen peroxide, metal peroxides, for example nickel peroxide, percarbonic acid and its salts or organic peracids, for example m-chloroperbenzoic acid, phthalomonoperacid or peracetic acid, or their salts, oxidising oxy-acids or their salts or anhydrides, such as hypohalogenous acids and their salts, for example sodium hypochlorite, halogen-containing acids and their salts, for example iodic acids, periodic acids, potassium iodate, sodium periodate or potassium chlorate, nitric acid or nitrous acid and their salts and anhydrides, for example potassium nitrate, sodium nitrite, nitric oxide, dinitrogen trioxide or nitrogen dioxide, or oxidising heavy metal compounds, such as chromium(VI), chromium(IV), manganese(IV), manganese(VII), silver(II), copper(II), mercury(II), vanadium(V) or bismuth(II) compounds, for example sodium dichromate, potassium dichromate, chromium trioxide, manganese dioxide, potassium permanganate, silver(II) oxide, copper(II) oxide, mercury oxide or bismuth oxide. Inert solvents are, for example, solvents that are inert towards the particular oxidising agent used, such as water, ketones, for example acetone, carboxylic acids and their anhydrides, for example acetic acid or acetic anhydride, halogenated hydrocarbons, for example tetrachloromethane, or aromatic or heteroaromatic substances, for example benzene or pyridine, or mixtures thereof.

Optionally esterified oxalo $X_{11}$ of the formula $-C(=O)-R$ can also be oxidised with decarbonylation taking place, for example in the presence of a suitable oxidising agent, if necessary while cooling or heating, for example at approximately from 0° to 100° C., in an inert solvent, in a closed vessel and/or under an inert gas, such as nitrogen. Suitable oxidising agents are, for example, per compounds, such as hydrogen peroxide or percarboxylic acids, for example percarbonic acid or organic percarboxylic acids, inter alia peracetic acid, performic acid, perbenzoic acid and the like, also oxyhalogen-acids and their salts, such as chloric acid or alkali metal chlorites, or oxidising metal compounds, such as silver oxide, potassium permanganate or chromium trioxide. Suitable solvents are, for example, optionally water-containing ketenes, such as acetone, or carboxylic acids, such as acetic acids.

The compounds of the formula XXI mentioned as starting materials, in which $X_{10}$ has the meaning indicated and represents, especially, a group $>CH-X_{11}$, can be manufactured according to methods known per se, for example by modifying some of the methods described above for the manufacture of compounds of the formula I, there being used in each case corresponding starting materials of the formulae IIa and IIb or IId and IIe, IIc or IIf, V, VII or XXXVII which contain a group $X_{10}$, preferably of the formula $>CH-X_{11}$, instead of the group $>CH-R$.

A preferred method consists, for example, in reacting a compound of the formula

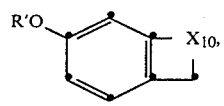 (XXII)

in which R' represents hydrogen, lower alkyl, such as methyl, or a hydroxy-protecting group R'', such as α-aralkyl, for example butyl, or tri-lower alkylsilyl, for example trimethylsilyl, or a group of the formula Ph—C(=O)—, in the presence of aluminium chloride or one of the other complex metal halides mentioned, with a compound Ph—C(=O)Hal (IId), R' preferably representing a lower alkyl radical and Hal representing halogen, for example chlorine.

The ketenes to be used as starting materials, that is to say compounds of the formula XXI in which $X_{10}$ represents a group of the formula $>C=C=O$, can also be manufactured by rearranging a corresponding α-diazoketone, for example a compound of the formula

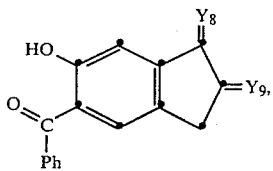

(XXIII)

in which one of the radicals $Y_8$ and $Y_9$ represents oxo and the other represents a group of the formula $=N_2$, this being carried out in customary manner with nitrogen being removed. If the rearrangement is carried out in the presence of water, an alcohol or ammonia or in the presence of an amine having at least one hydrogen atom, the ketene formed as primary product reacts further according to the invention without being isolated. The operation is advantageously carried out at elevated temperature, for example in a temperature range of approximately from 40° to 100° C., with illumination, for example with an ultra-violet light source, and/or in the presence of silver or silver compounds, for example silver, silver nitrate or silver oxide. Diazoketones of the formula XXIII can be obtained, for example, by reacting with hydrazine, for example at approximately 60° C. in ethanol, a compound of the formula

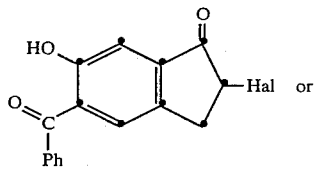 or (XXIV)

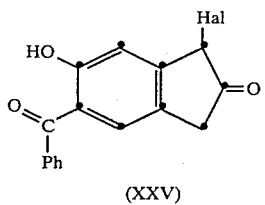

(XXV)

in which Hal represents halogen, obtainable from the corresponding indanone by halogenation, for example with N-bromosuccinimide, and oxidising the primary product, for example by treatment with manganese dioxide in chloroform.

Ketenes of the formula XXI in which $X_{10}$ represents a group of the formula $>C=C=O$ can also be obtained by reacting a diketone of the formula

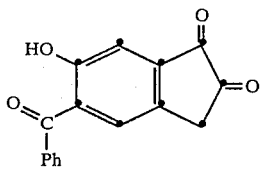

(XXVI)

with a sulphonic acid hydrazide, for example with p-toluenesulphonic acid hydrazide, and treating the resulting hydrazone XXIII ($Y_8$ or $Y_9=N-NH_2$ instead of $=N_2$) with alkali, for example sodium hydroxide solution, or by oximising the diketone by reaction with hydroxylamine and treating the oxime (in formula XXIII $Y_8$ or $Y_9$ is $=N-OH$ instead of $=N_2$) with chloroamine, or ammonia, and sodium hypochlorite. It is also possible to obtain the oximes mentioned by condensing a corresponding indanone with nitrous acid. Likewise, the hydrazones mentioned can be obtained by aminising a compound of the formula XXIV or XXV and diazotising the primary product in customary manner, for example with sodium nitrite and acetic acid.

Nitriles derived from acids of the formula I, for example compounds of the formula XXI in which $X_{10}$ represents a group $>CH-X_{11}$ and $X_{11}$ represents cyano, can also be manufactured by cyclising a compound of the formula

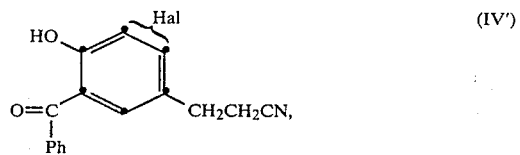

(IV')

or a salt thereof, in customary manner, for example by means of an alkali metal amide, such as potassium amide in ammonia or lithium N,N-diethylamide in tetrahydrofuran, or by reacting a compound of the formula

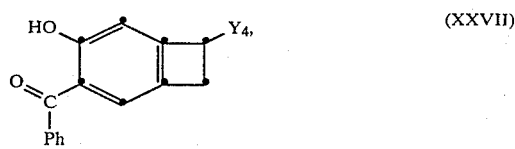

(XXVII)

or a phenolate salt thereof, in which $Y_4$ represents reactive esterified hydroxy, such as halogen or sulphonyloxy, for example iodine, bromine, chlorine or p-toluenesulphonyloxy, in customary manner with ammonium cyanide or a metal cyanide, for example sodium or potassium cyanide. Compounds of the formula XXVII can for their part be obtained, for example, by halogenating a corresponding benzocyclobutene compound, for example by treatment with a halogen or by means of N-bromo- or N-chloro-succinimide, or, in a corresponding benzocyclobutenone compound, reducing the oxo group to hydroxy and reacting this with a halogenating agent, such as phosphorus tribromide, or a sulphonic acid halide. It is, however, also possible to add hydrocyanic acid to a compound of the formula

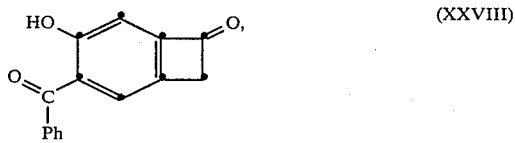

(XXVIII)

and, in the resulting α-cyanohydrin, to replace the hydroxy group reductively by hydrogen, optionally having previously removed the elements of water, for example in the manner indicated for corresponding compounds of the formula XIII.

The compounds of the formula XXVIII can be manufactured, for example, by cyclising a compound of the formula

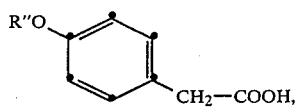 (XXIX)

in which R" represents, for example, lower alkyl, in customary manner, for example by acid treatment, such as by heating with sulphuric acid or polyphosphoric acid, and reacting the resulting compound of the formula

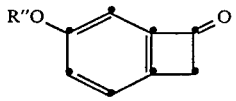 (XXX)

in the presence of aluminium trichloride with a compound of the formula

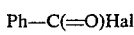 (IId).

Imino ethers and amidines to be used as starting materials are advantageously manufactured in situ by treating the corresponding nitrile with an alcohol or amine, customarily in the presence of a mineral acid, or by first of all converting the nitrile by mineral acid treatment into an imino ester and then subjecting this imino ester to alcoholysis or to ammonolysis or aminolysis. Hydrochloric or hydrobromic acid, especially, is suitable as the mineral acid. Ortho-anhydride esters can also be manufactured in an analogous manner by partial alcoholysis of ortho-anhydrides, for example tri-halomethyl compounds.

Compounds of the formula XXI in which $X_{10}$ represents a group of the formula $>CH-X_{11}$ and $X_{11}$ represents a 4,4- or 5,5-dimethyloxazin-2-yl or 4,6,6-trimethyldihydrooxazinyl group, acetalised formyl or an ortho-ester group can also be manufactured by reacting with one another in customary manner compounds of the formulae Ph—$Y_2$ (VI) and

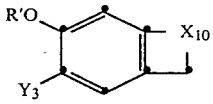 (XXXI)

in which one of the radicals $Y_2$ and $Y_3$, preferably $Y_2$, represents a metallic radical, such as an alkali metal atom or a halomagnesium group, and the other, preferably $Y_3$, represents carboxy that is optionally in salt form, for example in the form of an alkali metal salt, or functionally modified, such as esterified, or in the form of an anhydride, for example in the form of a halide, and R'O— represents free hydroxy or preferably hydroxy that is in salt form, for example in the form of an alkali or alkaline earth metal salt, or that is protected by a hydroxy-protecting group R", such as tri-lower alkylsilyl, for example trimethylsilyl, or α-aralkyl, for example benzyl, and, if appropriate, removing the hydroxy-protecting group R".

In a modification of this process, it is also possible to use as starting materials compounds of the formulae VI and XXI that contain cyano as the functionally modified carboxy group; there is thus obtained the imino derivative of the compound of the formula XXI, the imino group of which is hydrolysed to oxo in the course of the hydrolysis reaction.

Aldehydes, in enol ether form, of the formula XXI in which $X_{10}$ represents a group $>C=CH-OR_0$ can also be manufactured by reacting a compound of the formula

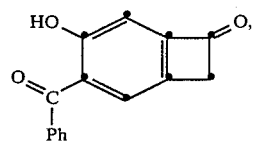 (XXXII)

or a phenolate salt thereof, in customary manner with a compound of the formula $(R_1)_3P=CH_2-OR_o$ (XXXIII)

in which the radicals $R_0$ and $R_1$ represent the same or different hydrocarbon radicals, for example $(R_1)_3P$ represents triphenylphosphino and $R_0$ represents lower alkyl.

From these it is possible, if desired, to free the aldehydes of the formula XXI in which $X_{10}$ represents a group of the formula $>CH-X_{11}$ and $X_{11}$ represents formyl that is optionally in hydrate form, by mild hydrolysis, advantageously with acid catalysis. It is also possible to hydrolyse acetals and acylals in which $X_{10}$ represents a group of the formula $>CH-X_{11}$ and $X_{11}$ represents acetalised or acylalised formyl to the corresponding aldehydes.

Compounds of the formula XXI in which $X_{10}$ represents a group of the formula $>CH-X_{11}$ and $X_{11}$ represents an optionally esterified oxalo group can also be obtained by condensing a compound of the formula

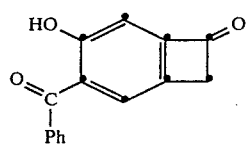 (XXVIII)

with hippuric acid in customary manner, for example in the presence of acetic anhydride, at approximately from 50° to 100° C., and hydrolysing the condensation product of the formula

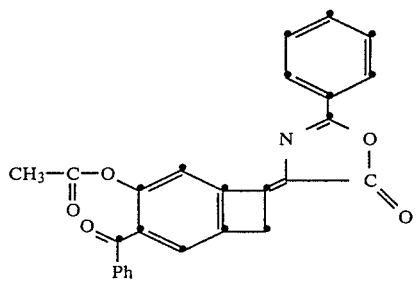 (XXXIV)

in customary manner, for example by treatment with sodium hydroxide solution.

Compounds of the formula XXI in which $X_{10}$ represents a group $>CH-X_{11}$ and $X_{11}$ represents formyl that is optionally in hydrate form can also be manufactured in situ under the conditions of their further oxidation by forming the formyl group by oxidation, for example of methyl, hydroxymethyl, aminomethyl or optionally substituted lower alkenyl, or of lower alkanoyl or lower alkenoyl each optionally substituted as indicated, or by freeing it, preferably hydrolytically, for example under acidic conditions, from one of its derivatives that contains, instead of formyl $X_{11}$, functionally modified formyl, such as an acetal, for example from di-lower alkoxy- or lower alkylenedioxy-methyl, acylate, for example from dihalomethyl, enol ethers, for example an enol-lower alkyl ether, enol esters, for example enol-lower alkanoic acid esters or enol esters with hydrohalic acids, oxime or enamine, for example enamine with pyrrolidine, piperidine, morpholine, thiomorpholine or a di-lower alkylamine. The acetals mentioned can be obtained, for example, by reacting a compound of the formula

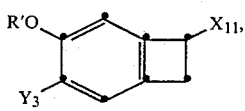 (XXXV)

in which R'O represents free hydroxy or preferably hydroxy that is in salt form, for example in the form of an alkali or alkaline earth metal salt, or that is protected by a hydroxy-protecting group R", such as tri-lower alkylsilyl, for example trimethylsilyl, or α-aralkyl, for example benzyl, with a compound of the formula $$Ph-Y_2 \quad (V)$$

in which $X_{11}$ represents acetalised formyl and one of the radicals $Y_2$ and $Y_3$ represents a metal group, for example of the formula —Li, —Na, —Mg/2, —Mg—Hal, —Cd/2, —CdHal or —ZnHal (Hal=halogen, such as chlorine, bromine or iodine), and the other represents a hydroxy group that is in salt form or is esterified, and, if necessary, removing the protecting group, for example by means of magnesium iodide. Analogously, compounds of the formula XXI in which $X_{10}$ represents a group of the formula $>C=_{12}$ and $X_{12}$ represents 1,3-dithian-2-ylidene can be obtained by reacting a compound of the formula

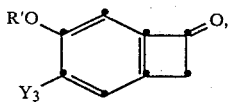 (XXXVI)

in which R' represents a hydroxy-protecting group, with 2-trimethylsilyl-1,3-dithian-2-yl-lithium, reacting the reaction product with a compound of the formula V and, if necessary, removing the protecting group.

The compounds of the formula I can also be manufactured by, in a compound of the formula

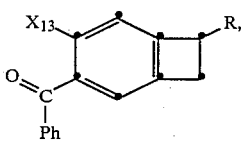 (XXXVII)

in which $X_{13}$ represents a group that can be converted into hydroxy, or in a salt thereof, converting $X_{13}$ into hydroxy and, if desired, converting the compound obtainable according to the process into a different compound of the formula I and/or converting a compound obtainable according to the process into a salt or converting a salt obtainable according to the process into the free compound or into a different salt.

Groups that can be converted into hydroxy are, for example, hydroxy groups protected in customary manner that, instead of the hydrogen atom, have as protecting groups groups that can be removed by neutral, acidic or basic solvolysis, especially hydrolysis, or by reduction. Protecting groups of this type, and also selective processes for their removal, that is to say for converting the protected hydroxy group into hydroxy, are sufficiently known in the literature.

In addition to other customary hydroxy-protecting groups, there come into consideration as groups $X_{13}$ that can be converted into hydroxy, for example, etherified hydroxy groups, such as lower alkoxy, tri-lower alkylsilyloxy or optionally substituted phenoxy-lower alkoxy groups, for example methoxy, trimethylsilyloxy or benzyloxy, especially protected hydroxy groups of the formula R"O— in which R" represents lower alkyl, for example methyl, α-aralkyl, for example benzyl, or tri-lower alkylsilyl, for example trimethylsilyl, esterified hydroxy groups, such as hydroxy groups esterified by inorganic acids or organic carboxylic acids, for example lower alkanoyloxy groups or groups of the formula Ph—C(=O)—O—, and also diazonium groups.

The conversion of these and similar groups $X_{13}$ is carried out in customary manner, for example by hydrolysis, if necessary in the presence of a hydrolysis agent, which is preferably acidic, a solvent or diluent or a solubiliser, while cooling or heating, for example in a temperature range of approximately from 0° to 120° C., and/or under an inert gas. Hydrolysis agents are, in addition to customary basic hydrolysis agents, such as alkali metal hydroxides, also acidic hydrolysis agents, for example Lewis acids, such as complex metal halides of the formula $M^nY_n$ (III) in which M represents an n-valent coordinatively unsaturated metal cation of the group IIa, IIb, IIIa, IIIb, IVb, Va or VIIIb of the Periodic Table of Elements, for example the magnesium, $zinc^{II}$, $boron^{III}$, $aluminium^{III}$, $gallium^{III}$, $tin^{IV}$, $titanium^{IV}$, $antimony^V$ or $iron^{III}$ or $iron^{VI}$ ion, and Y represents a halogen atom having an atomic number of up to and including 35, such as fluorine or chlorine, for example aluminium trichloride, or protonic acids, such as mineral acids, for example hydrochloric, hydrobromic or hydriodic acid, sulphuric acid, phosphoric acid or polyphosphoric acid, and also complex metal acids, for example hexachloroantimonic acid, tetrafluoroboric acid and the like, and, in the case of hydroxy groups $X_{13}$ esterified by organic carboxylic acids, also lower alkanoic acids, such as acetic acid. Solvents for the hydrolysis are, for example, water-miscible organic solvents.

Etherified hydroxy groups can be hydrolysed, for example, by treatment with aqueous hydriodic acid, with hydrobromic acid in highly concentrated, for example 98%, acetic acid or by treatment with aluminium trichloride. In a modification of this process, it is possible, for example, to treat compounds of the formulae

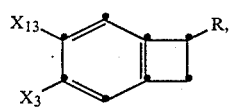 (XXXVIII)

in which $X_1$ represents a group of the formula —C(=O)—Z and Z represents anhydridised hydroxy, such as halogen, or a group of the formula Ph—C(=O)—O—, $X_{13}$ represents, for example, etherified hydroxy, such as lower alkoxy, and $X_3$ represents hydrogen, with a Lewis acid, such as with a complex metal halide of the formula $M^n Y_n$ (III), for example with aluminium trichoride, and to free the hydroxy group, by adding water, from the compound of the formula XXXVII which may be formed as primary product and in which $X_{13}$ represents, for example, etherified hydroxy.

It is also possible to treat a compound of the formula IIb in which $X_2$ represents optionally etherified hydroxy and $X_3$ represents hydrogen, in the presence of a protonic acid or one of the mentioned complex metal halides of the formula $M^n Y_n$ (III), with an excess of a compound of the formula IIa in which $X_1$ represents a group of the formula —C(=O)—Z and then to free the hydroxy group by hydrolysis from a compound of the formula XXXVII which may be formed and in which $X_{13}$ represents hydroxy esterified by an acid of the formula Ph—COOH.

In compounds of the formula XXXVII having as the group $X_{13}$ an optionally substituted α-phenyl-lower alkoxy group or another customary protected hydroxy group that can be cleaved by reduction, the hydroxy group can advantageously be freed by reduction. For example, hydrogenation can be carried out, that is to say with hydrogen in the presence of a hydrogenation catalyst, for example a palladium, platinum, nickel or rhodium catalyst, for example palladium-on-carbon or Raney nickel.

Furthermore, when using as starting materials compounds of the formula XXXVII in which $X_{13}$ represents hydroxy esterified by an organic carboxylic acid, the hydroxy group can be freed by transesterification, that is to say by treatment with an alcohol, for example lower alkanol, in the presence of an acidic or basic agent, such as a mineral acid, for example sulphuric acid, or an alkali metal hydroxide or alcoholate, for example sodium hydroxide or a sodium lower alkoxide.

The conversion of diazonium $X_{13}$ into hydroxy is carried out, for example, with the diazonium group being formed in situ, for example by diazotising a corresponding amino compound in which $X_{13}$ represents amino in customary manner and, without isolation, replacing the resulting diazonium salt by hydroxy by treatment with water, preferably at elevated temperature, for example at approximately from 40° to 120° C.

The starting materials of the formula XXXVII can be manufactured according to processes known per se, for example starting from compounds of the formula IIe, IIf or XXXIV, from compounds of the formula V, XI, XII, XIII, XIX, XX, XXI, XXIII, XXIV, XXV, XXVI, XXVII, XXVIII or XXXII which, instead of the phenolic hydroxy group, contain a group $X_{13}$ (except for diazonium with the inclusion of amino), from compounds of the formula II, IIb, IV, VII, VIII, X, XIV, XV, XVI, XVII, XVIII, XXII, XXXI, XXXV, XXXVI or XXXIX which, instead of the group R′O, contain a group $X_{13}$, or from compounds of the formula XXIX or XXX which, instead of the group R″O, contain a different group $X_{13}$, there being used, for example, the method indicated.

When carrying out the above-described methods of formation in practice, it may be advantageous to combine several similar reactions in the manner of a "one-pot reaction", for example to combine the oxidative conversion of a radical $X_4$ into a group Ph—C(=O)— in compounds of the formula V with the oxidative conversion of a radical $X_{10}$ into a group >CH—R in compounds of the formula XXI by using as starting material a corresponding compound of the formula

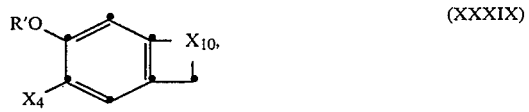

(XXXIX)

Likewise, the solvolytic conversion of a radical $X_4$ into a group Ph—C(=O)— in compounds of the formula V can be combined with the solvolytic conversion of a radical $X_{10}$ into a group >CH—R in compounds of the formula XXI and/or with the solvolytic conversion of $X_{13}$ into hydroxy in compounds of the formula XXXVII by using as starting material a corresponding compound of the formula XXXIX or a compound of the formula

(XL)

Furthermore, for example, the phenolic hydroxy group in compounds of the formulae V, XI, XII, XIII, XIX, XXI, XXIII, XXIV, XXV, XXVI, XXVII, XXVIII and XXXII can be protected intermediately by silylation, and the phenolic hydroxy group in compounds of the formulae XI, XII, XIII, XIX, XXI, XXIII, XXIV, XXV, XXVI, XXVII, XXVIII and XXXII can be protected intermediately by benzylation, acylation, alkylation or silylation, and the protecting group can be removed again after carrying out the reaction.

Compounds obtainable according to the process can also be converted into other compounds of the formula I.

For example, a free carboxy group R can be esterified to an esterified carboxy group R in customary manner, for example by treatment with a diazo-lower alkane or a tri-lower alkyloxonium, tri-lower alkylcarboxonium or di-lower alkylcarbenium salt, such as hexachloroantimonate or hexafluorophosphate, or especially by reaction with the corresponding alcohol or a reactive derivative, such as a carboxylic, phosphorous, sulphurous or carbonic acid ester, for example lower alkanecarboxylic acid ester, tri-lower alkyl phosphite, di-lower alkyl sulphite or a pyrocarbonate, or a mineral acid ester or sulphonic acid ester, for example the hydrochloric, hydrobromic, sulphuric, benzenesulphonic, toluenesulphonic or methanesulphonic acid ester, of the corresponding alcohol, or with an olefin derived therefrom.

The reaction with the corresponding alcohol itself can advantageously be carried out in the presence of an acidic catalyst, such as a protonic acid, for example hydrochloric, hydrobromic, sulphuric, phosphoric, boric, benzenesulphonic and/or toluenesulphonic acid, or a Lewis acid, for example boron trifluoride etherate, in an inert solvent, especially in an excess of the alcohol used and, if necessary, in the presence of a water-binding agent and/or with the removal of the water of reaction by distillation, for example azeotropic distillation, and/or at elevated temperature.

The reaction with a reactive derivative of the corresponding alcohol can be carried out in customary manner: when using a carboxylic, phosphorous, sulphurous or carbonic acid ester as starting material, the reaction is carried out, for example, in the presence of an acidic catalyst, such as one of those mentioned above, in an inert solvent, such as an aromatic hydrocarbon, for example in benzene or toluene, or an excess of the alcohol derivative used or of the corresponding alcohol. When using a mineral acid ester or a sulphonic acid ester as starting material, the acid to be esterified is advantageously used in the form of a salt, for example the sodium or potassium salt, and the operation is carried out, if necessary, in the presence of a basic condensation agent, such as an inorganic base, for example sodium, potassium or calcium hydroxide or carbonate, or a tertiary organic nitrogen base, for example triethylamine or pyridine, and/or in an inert solvent, such as one of the above-mentioned tertiary nitrogen bases, or a polar solvent, for example in dimethylformamide, and/or at elevated temperature.

The reaction with an olefin can be carried out, for example, in the presence of an acidic catalyst, for example a Lewis acid, for example boron trifluoride, a sulphonic acid, for example p-toluenesulphonic acid, or, especially, a basic catalyst, for example sodium or potassium hydroxide, advantageously in an inert solvent, such as an ether, for example diethyl ether or tetrahydrofuran.

A free carboxy group R can also be converted into an amidated carboxy group R by reaction in customary manner with ammonia or with an amine having at least one hydrogen atom, with dehydration of the intermediately formed ammonium salt, for example by azeotropic distillation with benzene or toluene or by dry heating.

The conversions described above of free carboxy groups R into esterified or amidated carboxy groups R can, however, also be carried out by first of all converting a compound of the formula I in which R represents carboxy in customary manner into a reactive derivative, for example by means of a halide of phosphorus or sulphur, for example by means of phosphorus trichloride or tribromide, phosphorus pentachloride or thionyl chloride, into an acid halide or, by reaction with a corresponding alcohol or amine, into a reactive ester, that is to say an ester having electron-attracting structures, such as an ester with phenol, thiophenol, p-nitrophenol or cyanomethyl alcohol, or into a reactive amide, for example an amide derived from imidazole or 3,5-dimethylpyrazole, and then reacting the resulting reactive derivative in customary manner, for example in the manner described below for the transesterification or conversion into one another of esterified and amidated carboxy groups R, with a corresponding alcohol, ammonia or the corresponding amine having at least one hydrogen atom to form the desired group R.

An esterified carboxy group R can be converted in customary manner into the free carboxy group R, for example by hydrolysis in the presence of a catalyst, for example a basic or acidic agent, such as a strong base, for example sodium or potassium hydroxide, or a mineral acid, for example hydrochloric acid, sulphuric acid or phosphoric acid, or into an amidated carboxy group R, for example by reaction with ammonia or the corresponding amine having at least one hydrogen atom.

An esterified carboxy group R can also be transesterified in customary manner to form a different esterified carboxy group R, for example by reaction with a metal salt, such as the sodium or potassium salt, of a corresponding alcohol or with the alcohol itself in the presence of a catalyst, for example a strong base, for example sodium or potassium hydroxide, or a strong acid, such as a mineral acid, for example hydrochloric acid, sulphuric acid or phosphoric acid, or an organic sulphonic acid, for example p-toluenesulphonic acid, or a Lewis acid, for example boron trifluoride etherate.

An amidated carboxy group R can be converted in customary manner into the free carboxy group R, for example by hydrolysis in the presence of a catalyst, for example a strong base, such as an alkali metal or alkaline earth metal hydroxide or carbonate, for example sodium or potassium hydroxide or carbonate, or a strong acid, such as a mineral acid, for example hydrochloric acid, sulphuric acid or phosphoric acid.

Depending on the starting materials and methods chosen, the novel compounds may be in the form of one of the possible isomers or in the form of a mixture thereof, for example, depending on the number of asymmetric carbon atoms, in the form of pure optical isomers, such as antipodes, or in the form of mixtures of isomers, such as racemates, mixtures of diastereoisomers or mixtures of racemates.

Resulting mixtures of diastereoisomers and resulting mixtures of racemates can be separated in known manner into the pure isomers, diastereoisomers or racemates on the basis of the physico-chemical differences between their components, for example by chromatography and/or fractional crystallisation.

Resulting racemates can also be resolved into the optical antipodes according to known methods, for example by recrystallisation from an optically active solvent, with the aid of micro-organisms, or by reaction of an acidic end product with an optically active base that forms salts with the racemic acid and separation of the salts obtained in this manner, for example on the basis of their different solubilities, into the diastereoisomers from which the antipodes can be freed by the action of suitable agents. Advantageously, the more active of the two antipodes is isolated.

Resulting free compounds of the formula I can be converted in a manner known per se into salts. Acidic compounds, for example those in which $R_4$ represents carboxy and/or $R_2$ and/or $R_3$ represents hydroxy, are converted into salts, for example with the corresponding base, and others are converted into salts, for example by treatment with an acid, for example one of the acids forming salts mentioned at the beginning, customarily in the presence of a solvent or diluent.

Resulting salts can be converted in a manner known per se into the free compounds, for example by treatment with an acidic reagent, such as a mineral acid, or a base, for example alkali hydroxide solution.

The compounds, including their salts, can also be obtained in the form of their hydrates or include the solvent used for crystallisation.

Owing to the close relationship between the novel compounds in free form and in the form of their salts, hereinbefore and hereinafter the free compounds and their salts are to be understood as meaning optionally also the corresponding salts and free compounds, respectively, where appropriate and expedient.

The invention also relates to those forms of the process according to which a compound obtainable as intermediate at any stage of the process is used as starting material and the remaining steps are carried out or a starting material is used in the form of a salt and/or racemate or antipode or, especially, is formed under the reaction conditions.

In the process of the present invention, it is preferable to use those starting materials which result in the compounds described at the beginning as being especially valuable. The invention relates also to novel starting materials and processes for their manufacture.

The pharmaceutical preparations according to the invention, which contain compounds of the formula I or pharmaceutically acceptable salts thereof, are for enteral, such as oral or rectal, and parenteral administration and also for topical administration to (a) warm-blooded animal(s) and contain the pharmacological active ingredient alone or together with a pharmaceutically acceptable carrier. The dosage of the active ingredient depends on the species of warm-blooded animal, age and individual condition and on the method of administration. In a normal case, the estimated daily dose for a warm-blooded animal weighing approximately 75 kg is, in the case of oral administration, approximately from 30–300 mg, advantageously divided into several equal partial doses.

The novel pharmaceutical preparations contain, for example, from approximately 10% to approximately 80%, preferably from approximately 20% to approximately 60%, of active ingredient. Pharmaceutical preparations according to the invention for enteral or parenteral administration are, for example, those in dosage unit form, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings that may be resistant to gastric juices, there being used, inter alia, concentrated sugar solutions that may contain gum arabic, talc, polyvinylpyrrolidone, polyethylene glycol and/or titanium dioxide, lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatin, and also soft sealed capsules consisting of gelatin and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical preparations, for example suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatin rectal capsules that contain a combination of the active ingredient and a base material; suitable base materials are, for example, liquid triglycerides, polyethylene glycols or paraffin hydrocarbons.

Suitable for parenteral administration are especially aqueous solutions of an active ingredient in water-soluble form, for example a water-soluble salt, also suspensions of the active ingredient, such as corresponding oily injection suspensions, suitable lipophilic solvents or vehicles, such as fatty oils, for example sesame oil, or synthetic fatty acid esters, for example ethyl oleate or triglycerides,being used, or aqueous injection suspensions that contain viscosity-increasing substances, for example sodium carboxymethylcellulose, sorbitol and/or dextran and optionally also stabilisers.

Suitable as topically administrable pharmaceutical preparations are especially creams, ointments, pastes, foams, tinctures and solutions that contain from approximately 0.5 to approximately 20% of active ingredient.

Creams are oil-in-water emulsions that contain more than 50% water. There are used as oily base especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable as emulsifiers are surface-active substances having predominantly hydrophilic properties, such as corresponding non-ionic emulsifiers, for example fatty acid esters of polyalcohols or ethylene oxide adducts thereof, such as polyglycerine fatty acid esters or polyoxyethylenesorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or stearyl alcohol. Additives to the aqueous phase are, inter alia, agents that reduce the drying-out of the creams, for example polyalcohols, such as glycerine, sorbitol, propylene glycol and/or polyethylene glycols, also preservatives, perfumes, etc.

Ointments are water-in-oil emulsions that contain up to 70%, but preferably from approximately 20% to approximately 50%, water or aqueous phases. Suitable as the fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes, etc.

Fatty ointments are anhydrous and contain as base especially hydrocarbons, for example paraffin, petroleum jelly and/or liquid paraffins, also natural or partially synthetic fats, for example coconut fatty acid triglyceride, or preferably hardened oils, for example hydrogenated groundnut or castor oil, also fatty acid partial esters of glycerine, for example glycerine mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium oxide or zinc oxide, also talc and/or aluminium silicates, the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. There are used as the oily phase, inter alia hydrocarbons, for example paraffin oil, fatty alcohols, for example cetyl alcohol, fatty acid esters, for example isopropyl myristate, and/or other waxes. There are used as emulsifiers, inter alia mixtures of emulsifiers having predominantly hydrophilic properties, such as polyoxyethylenesorbitan fatty acid esters (Tweens), and emulsifiers with predominantly lipophilic properties, such as sorbitan fatty acid esters (Spans). The customary additives, such as preservatives, etc., are also added.

Tinctures and solutions generally have an aqueous-ethanolic base to which are added, inter alia, polyalcohols, for example glycerine, glycols and/or polyethylene glycol, as humectants for reducing evaporation, and fat-restoring substances, such as fatty acid esters with lower polyethylene glycols, that is to say lipophilic substances that are soluble in the aqueous mixture, as a replacement for the fatty substances removed from the skin by the ethanol, and, if necessary, other adjuncts and additives.

The manufacture of the topically administrable pharmaceutical preparations is carried out in a manner known per se, for example by dissolving or suspending the active ingredient in the base or, if necessary, in a part thereof. When processing the active ingredient as a solution, it is generally dissolved in one of the two phases before emulsification; when processing the active ingredient as a suspension it is mixed with part of the base after emulsification and then added to the rest of the formulation.

The present invention relates also to the use of the compounds of the formula I and the salts of such compounds having salt-forming properties, preferably for the treatment of inflammation, chiefly inflammatory disorders of the rheumatic type, especially chronic arthritis.

The following Examples illustrate the invention described above but are not intended to limit its scope in any way. Temperatures are given in degrees Centigrade.

EXAMPLE 1

95.7 g of finely pulverised aluminium chloride are suspended in 180 ml of absolute methylene chloride. While stirring and cooling, 35 g of 5-methoxybenzocyclobutene-1-carboxylic acid methyl ester, dissolved in a small amount of methylene chloride, are added dropwise in such a manner that the temperature remains below 30°. At the same temperature, 50.5 g of benzoyl chloride are added dropwise thereto and the whole is subsequently heated at reflux for 4 hours. After cooling, the reaction mixture is poured onto 600 g of ice. The organic phase is separated off and the aqueous phase is extracted 3 times with 150 ml of methylene chloride each time. The combined organic phases are washed once with 250 ml of water, dried over magnesium sulphate and concentrated by evaporation. The excess benzoyl chloride is distilled off under a high vacuum and the residue is crystallised from ether/petroleum ether. 4-benzoyl-5-hydroxybenzocyclobutene-1-carboxylic acid methyl ester is obtained in the form of yellow crystals having a melting point of 75°–76°.

EXAMPLE 2

14 g of 4-benzoyl-5-hydroxybenzocyclobutene-1-carboxylic acid methyl ester are dissolved in 150 ml of ether and the solution is added to 62 ml of 2N aqueous sodium hydroxide solution and 25 ml of water. This mixture is vigorously stirred for 1 hour at room temperature. The ether phase is separated off and extracted once with 75 ml of water. The aqueous phase is washed once with 75 ml of ether. The combined aqueous phases are rendered acidic with 2N aqueous hydrochloric acid and extracted 3 times with 100 ml of methylene chloride each time. The combined methylene chloride extracts are dried over magnesium sulphate and concentrated by evaporation. Crystallisation of the residue from ether/petroleum ether yields 4-benzoyl-5-hydroxybenzocyclobutene-1-carboxylic acid in the form of yellow crystals having a melting point of 167°–169°.

EXAMPLE 3

26.6 g of finely pulverised aluminium chloride are suspended in 60 ml of methylene chloride. While stirring and while cooling slightly, 9.61 g of 5-methoxybenzocyclobutene-1-carboxylic acid methyl ester, dissolved in a small amount of methylene chloride, are added dropwise at room temperature. After stirring for 30 minutes at room temperature, 15.85 g of o-fluorobenzoyl chloride are added dropwise thereto and the resulting reaction mixture is heated at reflux for 4 hours. After cooling, the reaction mixture is poured onto ice and extracted thoroughly with methylene chloride. The combined organic phases are washed with water, dried over magnesium sulphate and concentrated by evaporation. The yellow oily residue (20 g) is chromatographed over 400 g of silica gel with methylene chloride. Fractions 7–16 (50 ml fractions) are combined and concentrated. The residue is crystallised from ether/petroleum ether. 4-(o-fluorobenzoyl)-5-hydroxybenzocyclobutene-1-carboxylic acid methyl ester is obtained in the form of yellow crystals having a melting point of 59°–61°.

EXAMPLE 4

12.1 g of 4-(m-chlorobenzoyl)-5-hydroxybenzocyclobutene-1-carboxylic acid methyl ester are dissolved in 120 ml of ether; 100 ml of 2N aqueous sodium hydroxide solution are added and the whole is stirred well for 15 minutes at room temperature. The ether phase is separated off and washed with water. The strongly yellow-coloured aqueous phase is washed with ether. The combined aqueous phases are rendered acidic with concentrated hydrochloric acid and extracted thoroughly with methylene chloride. The combined methylene chloride extracts are dried over magnesium sulphate and concentrated by evaporation. Crystallisation of the residue from ether/petroleum ether yields 4-(m-chlorobenzoyl)-5-hydroxybenzocyclobutene-1-carboxylic acid in the form of yellow crystals having a melting point of 138°–139°.

EXAMPLE 5

28.26 g of aluminium trichloride are suspended in 70 ml of dichloromethane and, over a period of 15 minutes, 10.19 g of 5-methoxybenzocyclobutene-1-carboxylic acid methyl ester are added dropwise at from 20° to 30°. Stirring is carried out for 30 minutes, 20.8 g of m-methylthiobenzoyl chloride are added dropwise over a period of 20 minutes and the whole is stirred for 4 hours at room temperature, poured into a mixture of 200 g of ice, 20 ml of concentrated hydrochloric acid and 200 ml of water, stirred for 30 minutes and extracted by shaking twice with 50 ml of dichloromethane each time and once with 50 ml of a mixture of trichloromethane and methanol (3:1). The organic phases are combined, washed twice with water, dried over magnesium sulphate, treated with kieselguhr and concentrated by evaporation. Chromatography over silica gel using hexane/ethyl acetate (4:1) as eluant yields 4-(m-methylthiobenzoyl)-5-hydroxybenzocyclobutene-1-carboxylic acid methyl ester in the form of a yellow oil.

EXAMPLE 6

In a manner analogous to that described in Example 5, starting from 37.12 g of aluminium trichloride, 13.42 g of 5-methoxybenzocyclobutene-1-carboxylic acid methyl ester and 26.05 g of o-methylthiobenzoyl chloride there is obtained 4-(o-methylthiobenzoyl)-5-hydroxybenzocyclobutene-1-carboxylic acid methyl ester in the form of a viscous yellow oil.

EXAMPLE 7

In a manner analogous to that described in Example 5, starting from 26.6 g of aluminium trichloride, 9.61 g of 5-methoxybenzocyclobutene-1-carboxylic acid methyl ester and 17.56 g of p-cyanobenzoyl chloride there is obtained 4-(p-cyanobenzoyl)-5-hydroxybenzocyclobutene-1-carboxylic acid methyl ester having a melting point of 113°–114°.

EXAMPLE 8

In a manner analogous to that described in Example 5, starting from 26.6 g of aluminium trichloride, 9.61 g of 5-methoxybenzocyclobutene-1-carboxylic acid methyl ester and 20.95 g of 2,4-dichlorobenzoyl chloride there is obtained 4-(2,4-dichlorobenzoyl)-5-hydroxybenzocyclobutene-1-carboxylic acid methyl ester having a melting point of 99°–100°.

EXAMPLE 9

In a manner analogous to that described in Example 5, starting from 26.6 g of aluminium trichloride, 9.61 g of 5-methoxybenzocyclobutene-1-carboxylic acid methyl ester and 20.95 g of 3,4-dichlorobenzoyl chloride there is obtained 4-(3,4-dichlorobenzoyl)-5-hydroxybenzocyclobutene-1-carboxylic acid methyl ester having a melting point of 95°–96°.

EXAMPLE 10

5.71 g of 4-(o-methylthiobenzoyl)-5-hydroxybenzocyclobutene-1-carboxylic acid methyl ester are dissolved in 70 ml of ether; 45 ml of 2N sodium hydroxide solution are added and stirring is carried out for 1 hour at room temperature. The aqueous phase is separated off and the ether phase is extracted by shaking twice with 25 ml of water each time. The aqueous phases are combined, acidified with 2N hydrochloric acid and extracted three times with 50 ml of dichloromethane each time. The extracts are combined, washed with water, dried over magnesium sulphate and concentrated by evaporation. After recrystallisation of the residue from dichloromethane/hexane, 4-(o-methylthiobenzoyl)-5-hydroxybenzocyclobutene-1-carboxylic acid is obtained having a melting point of 177°–178°.

EXAMPLE 11

In a manner analogous to that described in Example 10, starting from 4.9 g of 4-(m-methylthiobenzoyl)-5-hydroxybenzocyclobutene-1-carboxylic acid methyl ester there is obtained 4-(m-methylthiobenzoyl)-5-hydroxybenzocyclobutene-1-carboxylic acid having a melting point of 122°–124°.

EXAMPLE 12

3.0 g of 4-($\alpha$-hydroxybenzyl)-5-hydroxybenzocyclobutene-1-carboxylic acid are dissolved in 30 ml of dichloromethane and over a period of 10 minutes, while stirring, 30 g of pyridinium dichromate in 100 ml of dichloromethane are added dropwise thereto. Stirring is then carried out for 7 hours at room temperature, and the mixture is decanted off from the black residue, filtered over silica gel, concentrated to dryness by evaporation and crystallised from ether/hexane. 4-benzoyl-5-hydroxybenzocyclobutene-1-carboxylic acid is obtained having a melting point of 167°–169°.

The starting material can be manufactured, for example, as follows:

3.84 g of 5-methoxybenzocyclobutene-1-carboxylic acid methyl ester are dissolved in 20 ml of dichloromethane, the whole is cooled to 0° and there are added dropwise thereto at from 0° to 5° firstly 3.16 g of titanium tetrachloride over a period of 3 minutes and then 3.83 g of dichlorodimethyl ether ($Cl_2CHOCH_3$) over a period of 20 minutes. The whole is then stirred for 5 minutes at from 0° to 5°, gradually heated to room temperature and then stirred for 15 minutes at 35°. The mixture is then left to cool to room temperature and poured onto 25 g of ice; the organic phase is separated off, the aqueous phase is then shaken three times with 10 ml of dichloromethane each time and the organic phases are combined, washed three times with 15 ml of ice-water each time, dried over magnesium sulphate, concentrated to dryness by evaporation and chromatographed over silica gel using dichloromethane as eluant. 4-formyl-5-methoxybenzocyclobutene-1-carboxylic acid methyl ester is obtained in the form of a colourless oil.

1.6 g thereof are dissolved in 25 ml of ether; 19 ml of 2N sodium hydroxide solution are added and the whole is stirred vigorously for 20 minutes at room temperature. The ether phase is separated off and the aqueous phase is acidified slightly with 2N hydrochloric acid, extracted by shaking twice with 50 ml each time of a mixture of dichloromethane and ethyl acetate (4:1), washed with a small amount of ice-water, dried over magnesium sulphate and concentrated to dryness by evaporation. 4-formyl-5-methoxybenzocyclobutene-1-carboxylic acid is obtained in the form of a yellowish oil.

0.91 g thereof is dissolved in 5 ml of tetrahydrofuran and the solution is added dropwise to a freshly prepared, boiling solution of phenylmagnesium bromide (prepared from 0.39 g of magnesium and 2.51 g of bromobenzene in 10 ml of tetrahydrofuran). The whole is heated at reflux while stirring for 90 minutes, left to cool to room temperature and there are added thereto 20 g of ice and then saturated ammonium chloride solution until the turbidity disappears. The organic phase is separated off and the aqueous phase is extracted by shaking twice with ethyl acetate. The organic phases are combined, washed in succession with 40 % sodium bisulphite solution, saturated sodium bicarbonate solution and water, dried over magnesium sulphate and concentrated by evaporation. 4-(α-hydroxybenzyl)-5-methoxybenzocyclobutene-1-carboxylic acid is obtained which has a melting point of 143°–146° and which can be converted in a manner analogous to that described in Example 20 into 4-(α-hydroxybenzyl)-5-hydroxybenzocyclobutene-1-carboxylic acid.

EXAMPLE 13

10.65 g of 4-(2,6-dichlorobenzoyl)-5-hydroxybenzocyclobutene-1-carbonitrile are suspended in a mixture of 100 ml of concentrated hydrochloric acid and 100 ml of acetic acid and stirring is carried out for 4 hours at 100°. The whole is left to cool to room temperature, filtered with suction, washed thoroughly with water, left to dry in the air and recrystallised from trichloromethane/hexane with the addition of a small amount of methanol. 4-(2,6-dichlorobenzoyl)-5-hydroxybenzocyclobutene-1-carboxylic acid is obtained having a melting point of 202°–203°.

The starting material can be manufactured, for example, as follows:

While stirring at from 20° to 30°, 7.96 g of 5-methoxybenzocyclobutene-1-carbonitrile in 40 ml of dichloromethane are added dropwise to a suspension of 26.6 g of aluminium trichloride in 60 ml of dichloromethane. Stirring is carried out for 30 minutes at from 20° to 30° and then, over a period of 15 minutes, 20.95 g of 2,6-dichlorobenzoyl chloride are added dropwise thereto and the whole is stirred for 4 hours at room temperature and then poured into a mixture of 500 g of ice-water and 10 ml of concentrated hydrochloric acid. Stirring is then carried out for 30 minutes, 200 ml of trichloromethane are added, the whole is vigorously shaken and the organic phase is separated off, washed several times with semiconcentrated hydrochloric acid, dried over magnesium sulphate, concentrated to dryness by evaporation and recrystallised from dichloromethane/hexane. 4-(2,6-dichlorobenzoyl)-5-hydroxybenzocyclobutene-1-carbonitrile is obtained having a melting point of 174°–175°.

EXAMPLE 14

20 ml of concentrated hydrochloric acid and 10 ml of Cellosolve are added to 2 g of 4-(2,6-dichlorobenzoyl)-5-hydroxybenzocyclobutene-1-carbonitrile and stirring is carried out for 2 days at room temperature. 100 ml of water are added with stirring and the whole is filtered with suction and recrystallised from ether/hexane. 4-(2,6-dichlorobenzoyl)-5-hydroxybenzocyclobutene-1-carboxamide is obtained having a melting point of 174°.

EXAMPLE 15

2 g of 4-(2,6-dichlorobenzoyl)-5-hydroxybenzocyclobutene-1-carboxamide in 20 ml of acetic acid and 20 ml of concentrated hydrochloric acid are stirred for 4 hours at 95°–100°. The mixture is left to cool, filtered with suction, washed with water and recrystallised from trichloromethane/hexane. 4-(2,6-dichlorobenzoyl)-5-hydroxybenzocyclobutene-1-carboxylic acid is obtained having a melting point of 202°–203°.

EXAMPLE 16

2 g of 4-(2,6-dichlorobenzoyl)-5-hydroxybenzocyclobutene-1-carbonitrile are dissolved in 50 ml of ethanol, the whole is cooled to 0° and, while stirring at 0°, 10 g of 30% hydrogen peroxide are added dropwise thereto. 1.0 ml of 30% sodium hydroxide solution is then added slowly dropwise thereto and stirring is carried out for 6 hours at room temperature. The whole is neutralised with 6N hydrochloric acid and extracted thoroughly by shaking with 250 ml of dichloromethane. The organic phase is dried over magnesium sulphate and concentrated to dryness by evaporation. After recrystallisation from ether/hexane, 4-(2,6-dichlorobenzoyl)-5-hydroxybenzocyclobutene-1-carboxamide is obtained having a melting point of 174°–175°.

EXAMPLE 17

Over a period of 15 minutes, 4.86 g of 4-(2,6-dichlorobenzoyl)-5-hydroxybenzocyclobutene-1-carboxylic acid chloride are added dropwise, while stirring, to 15 ml of a 2.5 % solution of ammonia in dichloromethane. Stirring is carried out for 7 hours at room temperature, small amounts of a finely crystalline precipitate are filtered off and the filtrate is concentrated to dryness by evaporation, chromatographed over silica gel using dichloromethane/methanol (15:1) as eluant and recrystallised from ether/hexane. 4-(2,6-dichlorobenzoyl)-5-hydroxybenzocyclobutene-1-carboxamide is obtained having a melting point of 174°.

The starting material can be manufactured, for example, as follows:

3.37 g of 4-(2,6-dichlorobenzoyl)-5-hydroxybenzocyclobutene-1-carboxylic acid are suspended in 100 ml of toluene; 0.1 ml of dimethylformamide and 1.64 g of thionyl chloride are added and the whole is heated to 80°, stirred for 2 hours at 80°–90° and concentrated to dryness by evaporation under reduced pressure. 4-(2,6-dichlorobenzoyl)-5-hydroxybenzocyclobutene-1-carboxylic acid chloride is obtained which can be used without being further treated.

EXAMPLE 18

5.0 g of 4-(o-fluorobenzoyl)-5-methoxybenzocyclobutene-1-carboxylic acid methyl ester are dissolved in 100 ml of dichloromethane; 6.4 g of aluminium trichloride are added and the whole is heated at boiling for 4 hours while stirring. The mixture is poured onto ice;

20 ml of concentrated hydrochloric acid are added and the whole is extracted by shaking twice with 100 ml of dichloromethane each time. The organic phases are combined, washed with water, dried over magnesium sulphate and concentrated to dryness by evaporation. The residue is chromatographed over silica gel and recrystallised from ether/hexane. 4-(o-fluorobenzoyl)-5-hydroxybenzocyclobutene-1-carboxylic acid methyl ester is obtained having a melting point of 72°–73°.

The starting material can be manufactured, for example, as follows:

While stirring at from 0 to 3°, 9.61 g of 5-methoxybenzocyclobutene-1-carboxylic acid methyl ester are added dropwise to a suspension, cooled to 0°, of 26.6 g of aluminium trichloride in 60 ml of dichloromethane. The whole is stirred for 30 minutes at 0°, 15.9 g of o-fluorobenzoyl chloride are added dropwise thereto and stirring is carried out for 2 hours at from 0° to 3°. The whole is then poured into a mixture of 100 g of ice-water and 5 ml of concentrated hydrochloric acid, extracted by shaking twice with 100 ml of dichloromethane each time, washed with water, dried over magnesium sulphate and concentrated to dryness by evaporation. The residue is taken up in a small amount of dichloromethane, petroleum ether is added until a precipitate begins to form and the whole is then cooled. The precipitate that has formed is filtered off with suction and the filtrate is concentrated by evaporation and chromatographed over silica gel using dichloromethane as eluant. After a small number of first runnings, 4-(o-fluorobenzoyl)-5-methoxybenzocyclobutene-1-carboxylic acid methyl ester is obtained having a melting point of 73°–74°.

EXAMPLE 19

1.0 g of 4-benzoyl-5-hydroxybenzocyclobutene-1-methanol is dissolved in 50 ml of acetic acid and then 4.0 g of chromium trioxide are added in portions. The whole is stirred for 16 hours at 40°, concentrated to dryness by evaporation under reduced pressure, taken up in 20 ml of water and extracted by shaking with 80 ml of dichloromethane. The organic phase is dried over magnesium sulphate and concentrated by evaporation. After recrystallisation of the residue from ether/hexane, 4-benzoyl-5-hydroxybenzocyclobutene-1-carboxylic acid is obtained having a melting point of 167°–169°.

The starting material can be manufactured, for example, as follows:

Over a period of 30 minutes, while stirring, a solution of 1.92 g of 5-methoxybenzocyclobutene-1-carboxylic acid methyl ester in 30 ml of ether is added dropwise to a suspension of 0.21 g of lithium aluminium hydride in 30 ml of ether. The whole is stirred for 1 hour, a further 1.0 g of lithium aluminium hydride is added and stirring is carried out for a further 2 hours. 5 ml of water and, after a short time, 12.5 ml of 2N sulphuric acid are added dropwise thereto, stirring is carried out for 30 minutes and the ether phase is separated off, shaken twice with ether, dried over magnesium sulphate and concentrated to dryness by evaporation. 5-methoxybenzocyclobutene-1-methanol is obtained in the form of a colourless oil.

1.64 g thereof are dissolved in 30 ml of dichloromethane, and 1.21 g of triethylamine are added. Over a period of 5 minutes, 0.94 g of acetyl chloride in 10 ml of dichloromethane is then added dropwise at from 10 to 20o Stirring is carried out for 5 hours at room temperature, water is added and the organic phase is separated off. The organic phase is washed with water, dried over magnesium sulphate and concentrated by evaporation. 1-acetoxymethyl-5-methoxybenzocyclobutene is obtained in the form of a colourless oil.

1.78 g thereof are dissolved in 20 ml of dichloromethane and, while stirring, the whole is introduced dropwise into a suspension of 4.6 g of aluminium trichloride in 40 ml of dichloromethane. Stirring is carried out for 30 minutes and then 2.4 g of benzoyl chloride, dissolved in 10 ml of dichloromethane, are added dropwise at from 20° to 30°. The whole is stirred for 4 hours at room temperature and then poured onto ice; 5 ml of concentrated hydrochloric acid are added, stirring is carried out for 30 minutes and the organic phase is separated off, washed three times with water, dried over magnesium sulphate and concentrated to dryness by evaporation. 1-acetoxymethyl-4-benzoyl-5-hydroxybenzocyclobutene is obtained in the form of a yellowish oil.

2.2 g thereof are dissolved in 80 ml of methanol; a solution of 1.5 g of potassium carbonate in 50 ml of water is added and stirring is carried out at room temperature for 6 hours. The whole is concentrated to dryness by evaporation under reduced pressure, taken up in 50 ml of water, extracted by shaking twice with 100 ml of dichloromethane each time, dried over magnesium sulphate, concentrated to dryness by evaporation and purified by chromatography on a silica gel column using dichloromethane/ethyl acetate (9:1) as eluant. 4-benzoyl-5-hydroxybenzocyclobutene-1-methanol is obtained in the form of a viscous, yellow oil.

EXAMPLE 20

5 g of 5-benzoyloxybenzocyclobutene-1-carboxylic acid methyl ester are dissolved in 50 ml of 1,2-dichloroethane; 11.8 g of aluminium trichloride are added and the whole is heated at boiling for 35 hours. The reaction mixture is poured onto ice, and 20 ml of concentrated hydrochloric acid are added. The organic phase is separated off and the aqueous phase is extracted by shaking twice with dichloromethane. The organic phases are combined, dried over magnesium sulphate and concentrated by evaporation. The residue is recrystallised from ether/hexane. 4-benzoyl-5-hydroxybenzocyclobutene-1-carboxylic acid methyl ester is obtained in the form of yellowish crystals having a melting point of 75°–76°.

The starting material can be manufactured, for example, as follows:

1000 ml of a 1-molar solution of boron tribromide in dichloromethane are poured over 19.5 g of 5-methoxybenzocyclobutene-1-carboxylic acid methyl ester and the whole is heated at reflux for 6 hours. The whole is concentrated to dryness by evaporation and extracted by shaking with a mixture of 2000 ml of dichloromethane and 1000 ml of water and the organic phase is separated off, washed with water, dried over magnesium sulphate and concentrated to dryness by evaporation. 5-hydroxybenzocyclobutene-1-carboxylic acid methyl ester is obtained in the form of white crystals having a melting point of 108°–109° (from ether/hexane).

27 g of 5-hydroxybenzocyclobutene-1-carboxylic acid methyl ester are dissolved in 2000 ml of dichloromethane and then 18 g of triethylamine are added. Over a period of 5 minutes, while stirring at 10°–20°, 25 g of benzoyl chloride are added in portions, stirring is carried out for 5 hours at room temperature, 200 ml of water are added and the organic phase is separated off, dried over magnesium sulphate and concentrated to dryness by evaporation. 5-benzoyloxybenzocyclobutene-1-carboxylic acid methyl ester is obtained in the form of a colourless, viscous oil.

EXAMPLE 21

In a manner analogous to that described in Examples 1, 3, 5, 12, 18 and 20, it is also possible to manufacture:

4-(o-chlorobenzoyl)-5-hydroxybenzocyclobutene-1-carboxylic acid methyl ester in the form of a yellow oil, 4-(m-chlorobenzoyl)-5-hydroxybenzocyclobutene-1-carboxylic acid methyl ester in the form of a yellow oil, 4-(m-methoxycarbonylbenzoyl)-5-hydroxybenzocyclobutene-1-carboxylic acid methyl ester, m.p. 109°–110°, 4-(o-fluorobenzoyl)-5-hydroxybenzocyclobutene-1-carboxamide, 4-(m-methylbenzoyl)-5-hydroxybenzocyclobutene-1-carboxylic acid methyl ester in the form of a yellow oil, 4-(p-chlorobenzoyl)-5-hydroxybenzocyclobutene-1-carboxylic acid methyl ester in the form of yellow crystals having a melting point of 82°–84°, 4-(p-methylbenzoyl)-5-hydroxybenzocyclobutene-1-carboxylic acid methyl ester in the form of yellow crystals having a melting point of 100-102o, 4-(2,6-dichlorobenzoyl)-5-hydroxybenzocyclobutene-1-carboxylic acid methyl ester, 4-(o-bromobenzoyl)-5-hydroxybenzocyclobutene-1-carboxylic acid methyl ester, oil, 4-(o-acetoxybenzoyl)-5-hydroxybenzocyclobutene-1-carboxylic acid methyl ester, 4-(o-trifluoromethylbenzoyl)-5-hydroxybenzocyclobutene-1-carboxylic acid methyl ester, 4-(m-trifluoromethylbenzoyl)-5-hydroxybenzocyclobutene-1-carboxylic acid methyl ester, 4-(p-methoxybenzoyl)-5-hydroxybenzocyclobutene-1-carboxylic acid methyl ester, 4-(o-methoxybenzoyl)-5-hydroxybenzocyclobutene-1-carboxylic acid methyl ester, 4-(2,6-dimethylbenzoyl)-5-hydroxybenzocyclobutene-1-carboxylic acid methyl ester, 4-(2,6-dimethoxybenzoyl)-5-hydroxybenzocyclobutene-1-carboxylic acid methyl ester, 4-(o-methylbenzoyl)-5-hydroxybenzocyclobutene-1-carboxylic acid methyl ester.

EXAMPLE 22

In a manner analogous to that described in Examples 2, 4, 10, 12, 13, 15 and 19, it is also possible to manufacture:

4-(o-chlorobenzoyl)-5-hydroxybenzocyclobutene-1-carboxylic acid in the form of pale yellow crystals having a melting point of 151°–152°, 4-(m-methylbenzoyl)-5-hydroxybenzocyclobutene-1-carboxylic acid in the form of yellow crystals having a melting point of 142°–144°, 4-(p-chlorobenzoyl)-5-hydroxybenzocyclobutene-1-carboxylic acid in the form of yellow crystals having a melting point of 181°–183°, 4-(p-methylbenzoyl)-5-hydroxybenzocyclobutene-1-carboxylic acid in the form of yellow crystals having a melting point of 199°–201°, 4-(o-methylbenzoyl)-5-hydroxybenzocyclobutene-1-carboxylic acid having a melting point of 120.5°–121°, 4-(o-fluorobenzoyl)-5-hydroxybenzocyclobutene-1-carboxylic acid having a melting point of 138°–139°, 4-(2,4-dichlorobenzoyl)-5-hydroxybenzocyclobutene-1-carboxylic acid, m.p. 180°–181°, 4-(3,4-dichlorobenzoyl)-5-hydroxybenzocyclobutene-1-carboxylic acid, m.p. 189°–190°, 4-(o-bromobenzoyl)-5-hydroxybenzocyclobutene-1-carboxylic acid, m.p. 157°–158°, 4-(o-acetoxybenzoyl)-5-hydroxybenzocyclobutene-1-carboxylic acid, 4-(o-trifluoromethylbenzoyl)-5-hydroxybenzocyclobutene-1-carboxylic acid, 4-(m-trifluoromethylbenzoyl)-5-hydroxybenzocyclobutene-1-carboxylic acid, 4-(o-methoxybenzoyl)-5-hydroxybenzocyclobutene-1-carboxylic acid, 4-(p-methoxybenzoyl)-5-hydroxybenzocyclobutene-1-carboxylic acid, 4-(o-cyanobenzoyl)-5-hydroxybenzocyclobutene-1-carboxylic acid, m.p. 164°–165°, 4-(2,6-dimethylbenzoyl)-5-hydroxybenzocyclobutene-1-carboxylic acid, and 4-(2,6-dimethoxybenzoyl)-5-hydroxybenzocyclobutene-1-carboxylic acid.

EXAMPLE 23

Tablets each containing 25 mg of active ingredient, for example 4-benzoyl-5-hydroxybenzocyclobutene-1-carboxylic acid or a salt, for example the sodium salt, thereof, can be manufactured as follows:

| Constituents (for 1000 tablets): | |
| --- | --- |
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are first of all forced through a sieve having a mesh width of 0.6 mm. The active ingredient, the lactose, the talc, the magnesium stearate and half of the starch are then mixed. The other half of the starch is suspended in 40 ml of water and this suspension is added to a boiling solution of the polyethylene glycol in 100 ml of water and the mixture, if necessary with the addition of water, is granulated. The granulate is dried overnight at 35°, forced through a sieve having a mesh width of 1.2 mm and compressed to form tablets approximately 6mm in diameter that are concave on both sides.

In an analogous manner, it is also possible to manufacture tablets each containing 25 mg of a different compound of the formula I selected from those mentioned in Examples 1 to 22, it being possible for compounds in which R is carboxy also to be in the form of salts with bases, for example in the form of the sodium salt.

EXAMPLE 24

Tablets for chewing each containing 30 mg of active ingredient, for example 4-benzoyl-5-hydroxybenzocyclobutene-1-carboxylic acid or a salt, for example the sodium salt, thereof, can be manufactured, for example, as follows:

| Composition (for 1000 tablets): | |
|---|---|
| active ingredient | 30.0 g |
| mannitol | 267.0 g |
| lactose | 179.5 g |
| talc | 20.0 g |
| glycine | 12.5 g |
| stearic acid | 10.0 g |
| saccharine | 1.0 g |
| 5% gelatin solution | q.s. |

Manufacture

All the solid ingredients are first of all forced through a sieve having a mesh width of 0.25 mm. The mannitol and the lactose are mixed, granulated with the addition of gelatin solution, forced through a sieve having a mesh width of 2 mm, dried at 50° and forced through a sieve having a mesh width of 1.7 mm. The active ingredient, the glycine and the saccharine are carefully mixed; the mannitol, the lactose granulate, the stearic acid and the talc are added and the whole is mixed thoroughly and compressed to form tablets approximately 10 mm in diameter that are concave on both sides and have a breaking groove on the upper side.

In an analogous manner, tablets each containing 30 mg of a different compound of the formula I selected from those mentioned in Examples 1 to 22 can be manufactured, it being possible for compounds in which R is carboxy also to be in the form of salts with bases, for example in the form of the sodium salt.

EXAMPLE 25

Tablets each containing 100 mg of active ingredient, for example 4-benzoyl-5-hydroxybenzocyclobutene-1-carboxylic acid or a salt, for example the sodium salt, thereof, can be manufactured as follows:

| Composition (for 1000 tablets): | |
|---|---|
| active ingredient | 100.0 g |
| lactose | 248.5 g |
| corn starch | 17.5 g |
| polyethylene glycol 6000 | 5.0 g |
| talc | 15.0 g |
| magnesium stearate | 4.0 g |
| demineralised water | q.s. |

Manufacture

The solid ingredients are first of all forced through a sieve having a mesh width of 0.6 mm. The active ingredient, the lactose, the talc, the magnesium stearate and half of the starch are then intimately mixed. The other half of the starch is suspended in 65 ml of water and this suspension is added to a boiling solution of the polyethylene glycol in 260 ml of water. The resulting paste is added to the pulverulent substances and the whole is mixed and granulated, if necessary with the addition of water. The granulate is dried overnight at 35°, forced through a sieve having a mesh width of 1.2 mm and compressed to form tablets approximately 10 mm in diameter that are concave on both sides and have a breaking notch on the upper side.

In an analogous manner, it is also possible to manufacture tablets containing 100 mg of a different compound of the formula I according to Examples 1 to 22, it being possible for compounds in which R is carboxy also to be in the form of salts with bases, for example in the form of the sodium salt.

We claim:

1. A novel substituted benzophenone of the formula

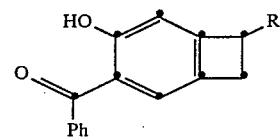

(I)

in which Ph represents unsubstituted or substituted phenyl and R represents free, esterified or amidated carboxy, or a salt thereof.

2. A compound according to patent claim 1, in which Ph represents phenyl that is unsubstituted or substituted by lower alkyl, lower alkoxy, lower alkylthio, lower alkanoyloxy, halogen, trifluoromethyl, carboxy, lower alkoxycarbonyl, cyano and/or nitro, and R represents carboxy, carboxy esterified by a lower aliphatic alcohol, or carbamoyl having as amino group amino that is unsubstituted or mono- or di-substituted by lower aliphatic radicals, or a salt thereof with a base.

3. A compound as claimed in claim 1, in which Ph represents phenyl that is unsubstituted or mono- or di-substituted by lower alkyl, lower alkoxy, lower alkanoyloxy, halogen, trifluoromethyl, cyano and/or nitro, and R represents carboxy, carboxy esterified by a lower aliphatic alcohol, or carbamoyl having as amino group amino that is unsubstituted or mono- or di-substituted by lower aliphatic radicals, or a salt thereof with a base.

4. A compound as claimed in claim 1, in which Ph represents phenyl that is unsubstituted or mono- or di-substituted by lower alkyl having up to and including 4 C-atoms, lower alkoxy having up to and including 4 C-atoms, lower alkanoyloxy having up to and including 4 C-atoms, halogen having an atomic number of up to and including 35, and/or trifluoromethyl, and R represents carboxy, lower alkoxycarbonyl having up to and including 5 C-atoms, or carbamoyl or N-lower alkylcarbamoyl having up to and including 5 C-atoms, or a salt thereof with a base.

5. A compound as claimed in claim 1, in which Ph represents phenyl that is unsubstituted or mono- or di-substituted by lower alkyl having up to and including 4 C-atoms, lower alkylthio having up to and including 4 C-atoms, lower alkoxycarbonyl having up to and including 4 C-atoms in the lower alkoxy moiety, halogen having an atomic number of up to and including 35, and/or cyano, and R represents carboxy or carbamoyl, also lower alkoxycarbonyl having up to and including 4 C-atoms in the lower alkoxy moiety, or a salt thereof with a base.

6. A compound as claimed in claim 1, in which Ph represents phenyl that is mono- or di-substituted by lower alkyl having up to and including 4 C-atoms or by halogen having an atomic number of up to and including 35, and R represents carboxy or carbamoyl, also lower alkoxycarbonyl having up to and including 4 C-atoms in the lower alkoxy moiety, or a salt thereof with a base.

7. A compound as claimed in claim 1, being 4-(Benzoyl)-5-hydroxybenzocyclobutene-1-carboxylic acid methyl ester.

8. A compound as claimed in claim 1, being 4-(o-Fluorobenzoyl-5-hydroxybenzocyclobutene-1-carboxylic acid methyl ester.

9. A compound as claimed in claim 1 being 4-(p-Chlorobenzoyl)-5-hydroxybenzocyclobutene-1-carboxylic acid or a salt thereof with a base.

10. A compound as claimed in claim 1 being 4-(2,6-Dichlorobenzoyl)-5-hydroxybenzocyclobutene-1-carboxylic acid or a salt thereof with a base.

11. A compound as claimed in claim 1 being 4-(p-Cyanobenzoyl)-5-hydroxybenzocyclobutene-1-carboxylic acid or a salt thereof with base.

12. A compound as claimed in claim 1 being 4-(2,6-Dimethylbenzoyl)-5-hydroxybenzocyclobutene-1-carboxylic acid or a salt thereof with a base.

13. A compound as claimed in claim 1 being 4-(o-Chlorobenzoyl)-5-hydroxybenzocyclobutene-1-carboxylic acid or a salt thereof with a base.

14. A compound as claimed in claim 1 being 4-(o-Fluorobenzoyl)-5-hydroxybenzocyclobutene-1-carboxylic acid or a salt thereof with a base.

15. A compound as claimed in claim 1 being 4-(o-Methylbenzoyl)-5-hydroxybenzocyclobutene-1-carboxylic acid or a salt thereof with a base.

16. A compound as claimed in claim 1 being 4-(2,4-Dichlorobenzoyl)-5-hydroxybenzocyclobutene-1-carboxylic acid or a salt thereof with a base.

17. A compound as claimed in claim 1 being 4-(o-Bromobenzoyl)-5-hydroxybenzocyclobutene-1-carboxylic acid or a salt thereof with a base.

18. A compound as claimed in claim 1 being 4-(o-Fluorobenzoyl)-5-hydroxybenzocyclobutene-1-carboxamide.

19. A pharmaceutical preparation containing a compound claimed in claim 1 in addition to customary pharmaceutical adjuncts and/or carriers.

20. Method for the treatment of painful inflammatory disorders, characterised in that a compound according to claim 1 is administered in the form of a pharmaceutically acceptable salt.

* * * * *

UNITED STATES PATENT AND TRADEMARK OFFICE
CERTIFICATE OF CORRECTION

PATENT NO. : 4,523,030
DATED : June 11, 1985
INVENTOR(S) : Georges Haas, Andreas von Sprecher, Pier G. Ferrini It is certified that error appears in the above—identified patent and that said Letters Patent is hereby corrected as shown below:

Column 22, last line should read

-- $Ph-X_1$ (IIa) and 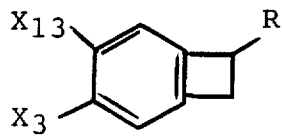 (XXXVIII) --.

Signed and Sealed this

Tenth Day of November, 1987

Attest:

DONALD J. QUIGG

*Attesting Officer*   *Commissioner of Patents and Trademarks*